US010385038B2

(12) United States Patent
Gong et al.

(10) Patent No.: US 10,385,038 B2
(45) Date of Patent: Aug. 20, 2019

(54) PYRIDINE SUBSTITUTED 2-AMINOPYRIDINE PROTEIN KINASE INHIBITOR CRYSTAL

(71) Applicants: Chia Tai Tianqing Pharmaceutical Group Co., Ltd., Lianyungang (CN); LIANYUNGANG RUNZHONG PHARMACEUTICAL CO., LTD., Lianyungang (CN); CENTAURUS BIOPHARMA CO., LTD., Beijing (CN)

(72) Inventors: Feng Gong, Lianyungang (CN); Xinlu Li, Lianyungang (CN); Rui Zhao, Lianyungang (CN); Xiquan Zhang, Lianyungang (CN); Xinhe Xu, Beijing (CN); Xijie Liu, Beijing (CN); Dengming Xiao, Beijing (CN); Yongxin Han, Beijing (CN)

(73) Assignees: CHIA TAI TIANQING PHARMACEUTICAL GROUP CO., LTD., Lianyungang (CN); LIANYUNGANG RUNZHONG PHARMACEUTICAL CO., LTD., Lianyungang (CN); CENTAURUS BIOPHARMA CO., LTD., Beijing (CN)

(*) Notice: Subject to any disclaimer, the term of this patent is extended or adjusted under 35 U.S.C. 154(b) by 0 days.

(21) Appl. No.: 15/749,075

(22) PCT Filed: Jul. 29, 2016

(86) PCT No.: PCT/CN2016/092269
§ 371 (c)(1),
(2) Date: Jan. 30, 2018

(87) PCT Pub. No.: WO2017/016514
PCT Pub. Date: Feb. 2, 2017

(65) Prior Publication Data
US 2018/0244649 A1    Aug. 30, 2018

(30) Foreign Application Priority Data
Jul. 30, 2015 (CN) .......................... 2015 1 0458524

(51) Int. Cl.
C07D 401/14       (2006.01)
A61K 31/496      (2006.01)
A61P 35/00        (2006.01)

(52) U.S. Cl.
CPC .......... *C07D 401/14* (2013.01); *A61K 31/496* (2013.01); *A61P 35/00* (2018.01); *C07B 2200/13* (2013.01)

(58) Field of Classification Search
CPC .. C07D 401/14; C07B 2200/13; A61K 31/496
See application file for complete search history.

(56) References Cited

U.S. PATENT DOCUMENTS 9,981,946 B2 * 5/2018 Gong ................... C07D 401/14
2016/0002205 A1   1/2016 Xiao et al.

FOREIGN PATENT DOCUMENTS

| CN | 103965161 A | 8/2014 |
|---|---|---|
| JP | 2008-510792 | 4/2008 |
| WO | WO 2006/021886 A1 | 3/2006 |
| WO | WO 2014/117718 A1 | 7/2014 |
| WO | WO 2014117718 A1 | 8/2014 |

OTHER PUBLICATIONS

International Search Report of the International Searching Authority for PCT/CN2016/092269; dated Nov. 4, 2016.
"Pharmacopoeia, XX J Guidelines for Hygroscopicity" is Appendix XIX J of the 2005 edition of Chinese Pharmacopoeia, p. A-250. Chinese Pharmacopoeia is edited by Chinese Pharmacopoeia Commission and published by China Medical Science Press.
English translation of "Pharmacopoeia, XX J Guidelines for Hygroscopicity" is Appendix XIX J of the 2005 edition of Chinese Pharmacopoeia, p. A-250. Chinese Pharmacopoeia is edited by Chinese Pharmacopoeia Commission and published by China Medical Science Press.
"Pharmacopoeia, XX C Guidelines for the Stability Testing of Drug Substances and Preparation" is Appendix XIX C, Part II of the 2010 edition of Chinese Pharmacopoeia, pp. A-239-A-242. Chinese Pharmacopoeia is edited by Chinese Pharmacopoeia Commission and published by China Medical Science Press.
English translation of "Pharmacopoeia, XX C Guidelines for the Stability Testing of Drug Substances and Preparation" is Appendix XIX C, Part II of the 2010 edition of Chinese Pharmacopoeia, pp. A-239-A-242. Chinese Pharmacopoeia is edited by Chinese Pharmacopoeia Commission and published by China Medical Science Press.

(Continued)

*Primary Examiner* — Erich A Leeser
(74) *Attorney, Agent, or Firm* — Tope-McKay & Associates

(57) ABSTRACT

The present invention discloses a crystal of citrate salt of pyridine-substituted 2-aminopyridine-based protein kinase inhibitors, in particular, to crystal of 5-((R)-1-(2,6-dichloro-3-fluorophenyl)ethoxy)-4'-methoxy-6'-((S)-2-methylpiperazin-1-yl)-3,3'-bipyridin-6-amine citrate salt, a method for preparation thereof, a crystalline composition and a pharmaceutical composition comprising the crystal, and further discloses the use of crystals of citrate salt of the compound of Formula I in protein kinase-related diseases. The crystals of citrate salt according to the present invention are superior to 5-((R)-1-(2,6-dichloro-3-fluorophenyl)ethoxy)-4'-methoxy-6'-((S)-2-methylpiperazin-1-yl)-3,3'-bipyridin-6-amine or other salts of 5-((R)-1-(2,6-dichloro-3-fluorophenyl)ethoxy)-4'-methoxy-6'-((S)-2-methylpiperazin-1-yl)-3,3'-bipyridin-6-amine in at least one aspect of bioavailability, hygroscopicity, stability, solubility, purity, ease of preparation, and the like.

11 Claims, 6 Drawing Sheets

(56) References Cited

OTHER PUBLICATIONS

Kruczynski, et al. (Anaplastic lymphoma kinase as a therapeutic target, A. 1127, Expert Opin. Ther. Targets (2012), 16(11), pp. 1127-1138.
Extended European Search Report dated Dec. 11, 2018 for counterpart European patent application No. 16829879.2.
Byrn Stephen et al: "Pharmaceutical solids: a strategic approach to regulatory consideration", Pharmaceutical Research, vol. 12, No. 7, Jan. 1, 1995, pp. 945-954.
First Office Action issued for corresponding Japanese Patent Application 2018-524523 dated Dec. 11, 2018.

* cited by examiner

PYRIDINE SUBSTITUTED 2-AMINOPYRIDINE PROTEIN KINASE INHIBITOR CRYSTAL

TECHNICAL FIELD

The present invention pertains to the field of pharmaceutical chemistry, and relates to a crystal of citrate salt of pyridine-substituted 2-aminopyridine-based protein kinase inhibitors, in particular, to a crystal of 5-((R)-1-(2,6-dichloro-3-fluorophenyl)ethoxy)-4'-methoxy-6'-((S)-2-methylpiperazin-1-yl)-3,3'-bipyridin-6-amine citrate salt, a method for preparation thereof, a crystalline composition and a pharmaceutical composition comprising the crystal, and use thereof in treatment of diseases associated with protein kinases.

BACKGROUND ART

Recent studies in molecular biology have shown that the cellular signal transduction pathway by the action of Protein Tyrosine Kinases (PTKs) plays a highly important role in tumorigenesis and development of tumors. Inhibition of tyrosine kinase activity can reduce activation of the cellular signal transduction pathway, so as to inhibit tumor cells from inducing survival and proliferation and produce an effect of treating cancers.

Anaplastic lymphoma kinase (ALK) is a receptor tyrosine kinase that belongs to the insulin receptor superfamily and plays an important role in tumor cell growth and development. The ALK gene may be fused with a variety of protein genes to express the ALK protein, and can have variations such as mutation and amplification. The oncogenic recombination of ALK gene on the short arm of Chromosome 2 in anaplastic large-cell lymphoma (ALCL) was described first in 1997, and later found in other malignancies, including diffuse large B-cell lymphoma and malignant histiocytosis, and also in many parenchymal tumors, including inflammatory myofibroblastoma, esophageal squamous epithelia cell carcinoma, neuroblastoma, and the recently proposed non-small cell lung cancer (NSCLC).

It was first reported in 2007 that the ALK gene may be fused to the EML4 gene to encode and produce ALK, thereby promoting lung cancer cell growth. The EML4-ALK fusion is caused by an insertion into the short arm of Chromosome 2, and so far a number of variants have been discovered. After testing, all of these fused genes were found to have biological functions, and their expression products are a kind of chimeric tyrosine kinase, which have been increasingly involved in reports on NSCLC since 2007.

Based on the discovery of the EML4-ALK fused gene and the distinct effect of ALK inhibitors displayed in the sub-group of population carrying it, NSCLC was divided into different subtypes according to different molecular pathologies, such as the EGFR mutant-, KRAS mutant-, and EML4-ALK gene fusion-types. In general NSCLC patients, the positive rate of the EML4-ALK fused gene is as low as about 3% to 7%. The EML4-ALK fused gene is mainly found in pulmonary adenocarcinoma of non-smokers. A study reported in 2010 showed that, in Chinese patients with pulmonary adenocarcinoma, the positive rate of the EML4-ALK fused gene, 16.13%, was significantly higher than that in Europe and United States; in pulmonary adenocarcinoma of non-smokers, the positive rate was 19.23%; and in pulmonary adenocarcinomas without EGFR or KRAS mutation, its mutation rate was as high as 42.8%.

Although a large number of compounds showing inhibitory activities against protein kinases have been investigated and some protein kinase inhibitors have been marketed for anti-tumor treatment, they can cause drug resistance. Therefore, there is an urgent need to develop new protein kinase inhibitors, for example, ALK inhibitors, for prophylaxis, alleviation and/or treatment of cancers mediated by protein kinases (e.g, ALK), such as ALK-positive non-small cell lung cancer (NSCLC).

WO2014117718 discloses 5-((R)-1-(2,6-dichloro-3-fluorophenyl)ethoxy)-4'-methoxy-6'-((S)-2-methylpiperazin-1-yl)-3,3'-bipyridin-6-amine (hereinafter, referred to as the compound of Formula I) and a method for preparation thereof.

Formula I

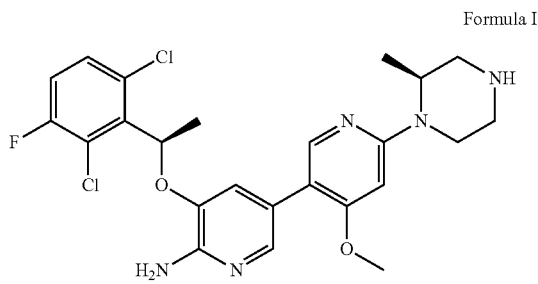 [SMILES: COc1cc(N2CCNC[C@@H]2C)ncc1-c1cnc(N)c(O[C@H](C)c2c(Cl)ccc(F)c2Cl)c1]

It is generally desirable that a medicament has good properties in terms of bioavailability, hygroscopicity, stability, solubility, purity, ease of preparation and the like, to meet the needs in production, storage and formulation of the medicament.

SUMMARY OF THE INVENTION

In an aspect, an embodiment of the present invention provides a crystal of 5-((R)-1-(2,6-dichloro-3-fluorophenyl)ethoxy)-4'-methoxy-6'-((S)-2-methylpiperazin-1-yl)-3,3'-bipyridin-6-amine citrate salt (hereinafter, referred to as a crystal of citrate salt of the compound of Formula I), which is superior to the compound of Formula I or other salts of the compound of Formula I in at least one of bioavailability, hygroscopicity, stability, solubility, purity, ease of preparation, and the like.

In another aspect, an embodiment of the present invention provides a method for preparation of the crystal of citrate salt of the compound of Formula I, comprising a step of contacting the compound of Formula I with citric acid.

In another aspect, an embodiment of the present invention provides a crystalline composition comprising the crystal of citrate salt of the compound of Formula I.

In yet another aspect, an embodiment of the present invention provides a crystal of citrate salt of the compound of Formula I, or a crystalline composition comprising the crystal, or a pharmaceutical composition comprising the crystal, or a pharmaceutical composition comprising the crystalline composition.

In a further aspect, an embodiment of the present invention provides use of a crystal of citrate salt of the compound of Formula I, or a crystalline composition comprising the crystal, or a pharmaceutical composition comprising the crystal, or a pharmaceutical composition comprising the crystalline composition, in the manufacture of a medicament for treatment and/or prophylaxis of a disease.

The crystal of citrate salt of the compound of Formula I according to the present invention, wherein a ratio of compound of Formula I to citric acid may be equal to or different from one. For example, the molar ratio of compound of Formula I to citric acid in the crystal of citrate salt of the compound of Formula I may be 1:0.5-4. In particular, the molar ratio of compound of Formula I to this pharmaceutically acceptable acid may be 1:0.5, 1:1, 1:1.5, 1:2, 1:2.5, 1:3, 1:3.5 or 1:4. In some specific embodiments of the present invention, the molar ratio of compound of Formula I to citric acid in the crystal of citrate salt of the compound of Formula I is 1:1.

According to a specific embodiment of the present invention, in the crystal of citrate salt of the compound of Formula I as provided according to the present invention, the crystal of citrate salt of the compound of Formula I comprises crystal form A of 5-((R)-1-(2,6-dichloro-3-fluorophenyl)ethoxy)-4'-methoxy-6'-((S)-2-methylpiperazin-1-yl)-3,3'-bipyridin-6-amine citrate salt (hereinafter, referred to as crystal form A of citrate salt of the compound of Formula I), crystal form B of 5-((R)-1-(2,6-dichloro-3-fluorophenyl)ethoxy)-4'-methoxy-6'-((S)-2-methylpiperazin-1-yl)-3,3'-bipyridin-6-amine citrate salt (hereinafter, referred to as crystal form B of citrate salt of the compound of Formula I), or crystal form C of 5-((R)-1-(2,6-dichloro-3-fluorophenyl)ethoxy)-4'-methoxy-6'-((S)-2-methylpiperazin-1-yl)-3,3'-bipyridin-6-amine citrate salt (hereinafter, referred to as crystal form C of citrate salt of the compound of Formula I).

In some specific embodiments of the present invention, in the crystal form A of citrate salt of the compound of Formula I, crystal form B of citrate salt of the compound of Formula I or crystal form C of citrate salt of the compound of Formula I, the molar ratio of compound of Formula I to citric acid is 1:1.

In an aspect, an embodiment of the present invention provides crystal form A of citrate salt of the compound of Formula I, characterized in that, in an X-ray powder diffraction pattern with Cu Kα radiation thereof, characteristic peaks are present at 2θ angles of about 12.78, 14.61, 17.63, 18.98, 21.42 and 23.47 degrees, preferably at 2θ angles of about 7.05, 9.48, 12.78, 14.61, 15.66, 17.63, 18.98, 21.42 and 23.47 degrees, more preferably at 2θ angles of about 5.73, 7.05, 9.48, 12.78, 13.76, 14.31, 14.61, 15.66, 17.63, 18.98, 21.42, 21.82, 23.47 and 25.68 degrees, even more preferably at 2θ angles of about 5.73, 7.05, 8.60, 9.48, 12.78, 13.76, 13.99, 14.31, 14.61, 15.66, 17.63, 18.98, 20.25, 20.82, 21.42, 21.82, 22.26, 22.49, 23.47, 25.68, 26.64 and 30.19 degrees, and most preferably at 2θ angles of about 5.73, 7.05, 8.60, 9.48, 12.78, 13.76, 13.99, 14.31, 14.61, 15.66, 16.68, 17.13, 17.63, 18.98, 20.25, 20.82, 21.42, 21.82, 22.26, 22.49, 23.47, 24.86, 25.68, 26.00, 26.64, 27.25, 28.04, 28.76, 29.64, 30.19, 31.33, 31.70, 32.64, 33.47, 33.74, 34.60, 35.72 and 38.44.

Furthermore, in an X-ray powder diffraction pattern with Cu Kα radiation of crystal form A of citrate salt of the compound of Formula I according to the present invention, the peak positions and intensities of the characteristic peaks are shown in the table below.

| No. | 2θ (degree) | Relative intensity (I/I$_0$) |
|---|---|---|
| 1 | 5.73 | 53.2 |
| 2 | 7.05 | 89.0 |
| 3 | 8.60 | 25.3 |
| 4 | 9.48 | 86.3 |
| 5 | 12.78 | 100.0 |
| 6 | 13.76 | 47.6 |
| 7 | 13.99 | 42.6 |

-continued

| No. | 2θ (degree) | Relative intensity (I/I$_0$) |
|---|---|---|
| 8 | 14.31 | 52.0 |
| 9 | 14.61 | 97.3 |
| 10 | 15.66 | 84.3 |
| 11 | 16.68 | 14.6 |
| 12 | 17.13 | 10.3 |
| 13 | 17.63 | 94.4 |
| 14 | 18.98 | 85.6 |
| 15 | 20.25 | 32.4 |
| 16 | 20.82 | 36.7 |
| 17 | 21.42 | 93.0 |
| 18 | 21.82 | 48.2 |
| 19 | 22.26 | 36.8 |
| 20 | 22.49 | 37.9 |
| 21 | 23.47 | 90.1 |
| 22 | 24.86 | 14.2 |
| 23 | 25.68 | 52.7 |
| 24 | 26.00 | 25.8 |
| 25 | 26.64 | 22.6 |
| 26 | 27.25 | 19.4 |
| 27 | 28.04 | 13.8 |
| 28 | 28.76 | 15.4 |
| 29 | 29.64 | 6.1 |
| 30 | 30.19 | 34.3 |
| 31 | 31.33 | 18.1 |
| 32 | 31.70 | 17.3 |
| 33 | 32.64 | 6.5 |
| 34 | 33.47 | 20.4 |
| 35 | 33.74 | 18.3 |
| 36 | 34.60 | 7.3 |
| 37 | 35.72 | 17.5 |
| 38 | 38.44 | 6.6 |

In a specific embodiment, crystal form A of citrate salt of the compound of Formula I according to the present invention is characterized by the X-ray powder diffraction pattern as shown in FIG. 1.

Without limitation, the differential scanning calorimetry (DSC) curve of crystal form A of citrate salt of the compound of Formula I according to the present invention has an absorption peak at about 195.9° C., and is specifically characterized by the DSC curve as shown in FIG. 4.

Without limitation, crystal form A of citrate salt of the compound of Formula I according to the present invention is characterized by the thermogravimetric analysis (TGA) curve as shown in FIG. 7.

Without limitation, the infrared absorption spectrum (IR) of crystal form A of citrate salt of the compound of Formula I according to the present invention has absorption peaks at about 3462.3 cm$^{-1}$, 2998.2 cm$^{-1}$, 1721.2 cm$^{-1}$, 1686.4 cm$^{-1}$, 1603.4 cm$^{-1}$, 1380.2 cm$^{-1}$ and 1201.8 cm$^{-1}$, preferably has absorption peaks at about 3462.3 cm$^{-1}$, 2998.2 cm$^{-1}$, 1721.2 cm$^{-1}$, 1686.4 cm$^{-1}$, 1603.4 cm$^{-1}$, 1567.7 cm$^{-1}$, 1491.3 cm$^{-1}$, 1460.3 cm$^{-1}$, 1412.1 cm$^{-1}$, 1380.2 cm$^{-1}$, 1344.3 cm$^{-1}$ and 1201.8 cm$^{-1}$, most preferably has absorption peaks at about 3462.3 cm$^{-1}$, 2998.2 cm$^{-1}$, 1721.2 cm$^{-1}$, 1686.4 cm$^{-1}$, 1603.4 cm$^{-1}$, 1567.7 cm$^{-1}$, 1491.3 cm$^{-1}$, 1460.3 cm$^{-1}$, 1412.1 cm$^{-1}$, 1380.2 cm$^{-1}$, 1344.3 cm$^{-1}$, 1277.3 cm$^{-1}$, 1246.6 cm$^{-1}$, 1201.8 cm$^{-1}$, 1180.8 cm$^{-1}$, 1162.3 cm$^{-1}$, 1071.5 cm$^{-1}$, 1050.6 cm$^{-1}$, 1022.7 cm$^{-1}$, 1002.1 cm$^{-1}$ and 815.2 cm$^{-1}$, and is specifically characterized by the infrared absorption spectrum (IR) as shown in FIG. 9.

In another aspect, an embodiment of the present invention provides crystal form B of citrate salt of the compound of Formula I, characterized in that, in an X-ray powder diffraction pattern with Cu Kα radiation thereof, characteristic peaks are present at 2θ angles of about 6.74, 12.62, 18.42, 22.96 and 25.22 degrees, preferably at 2θ angles of about 6.74, 7.19, 12.62, 16.42, 18.42, 22.65, 22.96 and 25.22 degrees, more preferably at 2θ angles of about 6.74, 7.19, 12.16, 12.62, 13.12, 13.77, 14.14, 16.42, 18.42, 22.02, 22.65, 22.96, 24.08, 25.22 and 27.45 degrees, and most preferably at 2θ angles of about 6.14, 6.74, 7.19, 10.50, 11.47, 12.16, 12.62, 13.12, 13.77, 14.14, 15.20, 16.42, 17.15, 18.42, 20.13, 21.18, 21.40, 22.02, 22.65, 22.96, 24.08, 25.22, 25.88, 27.45, 28.35, 30.45, 32.09, 32.79, 33.27, 33.88 and 34.92 degrees.

Furthermore, in an X-ray powder diffraction pattern with Cu Kα radiation of crystal form B of citrate salt of the compound of Formula I according to the present invention, the peak positions and intensities of the characteristic peaks are shown in the table below.

| No. | 2θ (degree) | Relative intensity (I/I$_0$) |
|---|---|---|
| 1 | 6.14 | 8.8 |
| 2 | 6.74 | 91.4 |
| 3 | 7.19 | 58.7 |
| 4 | 10.50 | 6.3 |
| 5 | 11.47 | 10.3 |
| 6 | 12.16 | 43.8 |
| 7 | 12.62 | 97.6 |
| 8 | 13.12 | 49.6 |
| 9 | 13.77 | 42.5 |
| 10 | 14.14 | 44.9 |
| 11 | 15.20 | 10.6 |
| 12 | 16.42 | 62.9 |
| 13 | 17.15 | 19.5 |
| 14 | 18.42 | 100 |
| 15 | 20.13 | 22.9 |
| 16 | 21.18 | 26.4 |
| 17 | 21.40 | 25.1 |
| 18 | 22.02 | 39.3 |
| 19 | 22.65 | 60.1 |
| 20 | 22.96 | 78.4 |
| 21 | 24.08 | 41.7 |
| 22 | 25.22 | 71.6 |
| 23 | 25.88 | 27.6 |
| 24 | 27.45 | 26.8 |
| 25 | 28.35 | 15.0 |
| 26 | 30.45 | 16.8 |
| 27 | 32.09 | 8.6 |
| 28 | 32.79 | 12.6 |
| 29 | 33.27 | 15.5 |
| 30 | 33.88 | 12.5 |
| 31 | 34.92 | 13.0 |

In a specific embodiment, crystal form B of citrate salt of the compound of Formula I according to the present invention is characterized by the X-ray powder diffraction pattern as shown in FIG. 2.

Without limitation, the differential scanning calorimetry (DSC) curve of crystal form B of citrate salt of the compound of Formula I according to the present invention has an absorption peak at about 194.3° C., and is specifically characterized by the DSC curve as shown in FIG. 5.

Without limitation, crystal form B of citrate salt of the compound of Formula I according to the present invention is characterized by the thermogravimetric analysis (TGA) curve as shown in FIG. 8.

Without limitation, the infrared absorption spectrum (IR) of crystal form B of citrate salt of the compound of Formula I according to the present invention has absorption peaks at about 2993.1 cm$^{-1}$, 1731.1 cm$^{-1}$, 1600.0 cm$^{-1}$, 1451.2 cm$^{-1}$, 1389.6 cm$^{-1}$, 1270.0 cm$^{-1}$ and 1200.4 cm$^{-1}$, preferably has absorption peaks at about 3490.2 cm$^{-1}$, 2993.1 cm$^{-1}$, 1731.1 cm$^{-1}$, 1684.0 cm$^{-1}$, 1600.0 cm$^{-1}$, 1686.4 cm$^{-1}$, 1489.5 cm$^{-1}$, 1451.2 cm$^{-1}$, 1389.6 cm$^{-1}$, 1270.0 cm$^{-1}$, 1248.7 cm$^{-1}$ and 1200.4 cm$^{-1}$, most preferably has absorption peaks at about 3490.2 cm$^{-1}$, 3310.8 cm$^{-1}$, 3063.4 cm$^{-1}$, 2993.1 cm$^{-1}$, 2841.9 cm$^{-1}$, 1731.1 cm$^{-1}$, 1684.0 cm$^{-1}$, 1600.0 cm$^{-1}$, 1686.4 cm$^{-1}$, 1489.5 cm$^{-1}$, 1451.2 cm$^{-1}$, 1403.7 cm$^{-1}$, 1389.6 cm$^{-1}$, 1343.3 cm$^{-1}$, 1316.3 cm$^{-1}$, 1270.0 cm$^{-1}$, 1248.7 cm$^{-1}$, 1224.5 cm$^{-1}$, 1200.4 cm$^{-1}$, 1031.9 cm$^{-1}$, 995.5 cm$^{-1}$ and 825.7 cm$^{-1}$, and is specifically characterized by the infrared absorption spectrum (IR) as shown in FIG. 10.

In yet another aspect, an embodiment of the present invention provides crystal form C of citrate salt of the compound of Formula I, characterized in that, in an X-ray powder diffraction pattern with Cu Kα radiation, characteristic peaks are present at 2θ angles of about 7.00, 12.78, 13.66, 15.64, 18.14 and 23.43 degrees, preferably at 2θ angles of about 7.00, 12.78, 13.66, 14.01, 14.56, 15.64, 17.58, 18.14, 18.89, 21.37 and 23.43 degrees, more preferably at 2θ angles of about 7.00, 9.48, 12.78, 13.66, 14.01, 14.56, 15.64, 17.58, 18.14, 18.89, 19.84, 20.83, 21.37, 21.76, 22.47, 23.43, 23.66, 24.23, 24.87, 25.61 and 30.16 degrees, and most preferably at 2θ angles of about 5.71, 6.43, 7.00, 8.54, 9.48, 11.22, 12.19, 12.78, 13.66, 14.01, 14.56, 15.64, 16.66, 16.99, 17.58, 18.14, 18.89, 19.84, 20.21, 20.83, 21.37, 21.76, 22.47, 23.43, 23.66, 24.23, 24.87, 25.61, 25.91, 26.55, 27.21, 28.00, 28.76, 30.16, 31.26, 31.69, 33.41, 33.71, 34.52 and 35.70 degrees.

Furthermore, in an X-ray powder diffraction pattern with Cu Kα radiation of crystal form C of citrate salt of the compound of Formula I according to the present invention, the peak positions and intensities of the characteristic peaks are shown in the table below.

| No. | 2θ (degree) | Relative intensity (I/I$_0$) |
|---|---|---|
| 1 | 5.71 | 14.8 |
| 2 | 6.43 | 11.0 |
| 3 | 7.00 | 100.0 |
| 4 | 8.54 | 7.5 |
| 5 | 9.48 | 28.8 |
| 6 | 11.22 | 8.4 |
| 7 | 12.19 | 17.2 |
| 8 | 12.78 | 55.0 |
| 9 | 13.66 | 69.2 |
| 10 | 14.01 | 52.1 |
| 11 | 14.56 | 38.4 |
| 12 | 15.64 | 41.9 |
| 13 | 16.66 | 14.8 |
| 14 | 16.99 | 15.3 |
| 15 | 17.58 | 38.9 |
| 16 | 18.14 | 44.9 |
| 17 | 18.89 | 35.0 |
| 18 | 19.84 | 11.9 |
| 19 | 20.21 | 19.4 |
| 20 | 20.83 | 20.0 |
| 21 | 21.37 | 37.2 |
| 22 | 21.76 | 24.6 |
| 23 | 22.47 | 26.2 |
| 24 | 23.43 | 39.0 |
| 25 | 23.66 | 29.9 |
| 26 | 24.23 | 19.9 |
| 27 | 24.87 | 18.8 |
| 28 | 25.61 | 31.3 |
| 29 | 25.91 | 18.7 |
| 30 | 26.55 | 9.0 |
| 31 | 27.21 | 10.4 |
| 32 | 28.00 | 10.3 |
| 33 | 28.76 | 11.5 |
| 34 | 30.16 | 16.8 |
| 35 | 31.26 | 8.9 |
| 36 | 31.69 | 8.9 |
| 37 | 33.41 | 8.3 |
| 38 | 33.71 | 9.4 |
| 39 | 34.52 | 4.8 |
| 40 | 35.70 | 8.1 |

In a specific embodiment, crystal form C of citrate salt of the compound of Formula I according to the present invention is characterized by the X-ray powder diffraction pattern as shown in FIG. 3.

Without limitation, the differential scanning calorimetry (DSC) curve of crystal form C of citrate salt of the compound of Formula I according to the present invention has an absorption peak at about 196.2° C., and is specifically characterized by the DSC curve as shown in FIG. 6.

Without limitation, the infrared absorption spectrum (IR) of crystal form C of citrate salt of the compound of Formula I according to the present invention has absorption peaks at about 3490.5 cm$^{-1}$, 2993.6 cm$^{-1}$, 1730.2 cm$^{-1}$, 1600.4 cm$^{-1}$, 1489.0 cm$^{-1}$, 1270.0 cm$^{-1}$ and 1200.8 cm$^{-1}$, preferably has absorption peaks at about 3490.5 cm$^{-1}$, 3299.9 cm$^{-1}$, 2993.6 cm$^{-1}$, 1730.2 cm$^{-1}$, 1683.6 cm$^{-1}$, 1600.4 cm$^{-1}$, 1489.0 cm$^{-1}$, 1451.5 cm$^{-1}$, 1380.0 cm$^{-1}$, 1270.0 cm$^{-1}$, 1247.8 cm$^{-1}$, 1200.8 cm$^{-1}$, 1031.8 cm$^{-1}$ and 826.1 cm$^{-1}$, most preferably has absorption peaks at about 3490.5 cm$^{-1}$, 3299.9 cm$^{-1}$, 3062.3 cm$^{-1}$, 2993.6 cm$^{-1}$, 2842.4 cm$^{-1}$, 1730.2 cm$^{-1}$, 1683.6 cm$^{-1}$, 1600.4 cm$^{-1}$, 1489.0 cm$^{-1}$, 1451.5 cm$^{-1}$, 1404.5 cm$^{-1}$, 1380.0 cm$^{-1}$, 1343.8 cm$^{-1}$, 1270.0 cm$^{-1}$, 1247.8 cm$^{-1}$, 1200.8 cm$^{-1}$, 1161.3 cm$^{-1}$, 1120.0 cm$^{-1}$, 1099.3 cm$^{-1}$, 1077.8 cm$^{-1}$, 1050.0 cm$^{-1}$, 1031.8 cm$^{-1}$, 995.7 cm$^{-1}$ and 826.1 cm$^{-1}$, and is specifically characterized by the infrared absorption spectrum as shown in FIG. 11.

According to the present invention, the instrument for X-ray powder diffraction spectrometry was a Bruker D2 X-ray diffractometer. Conditions and Method: 30 kv 10 mA, slit: 0.6/3/Ni/8, 2θ: 5 to 400, time[s]: 0.1, step size: 0.02°.

According to the present invention, the instrument for DSC spectrometry was METTLER TOLEDO DSC1. Conditions and Method: the temperature was increased by 10° C./min in the range of 30 to 300° C., and the DSC curve was scanned.

According to the present invention, the instrument for TGA spectrometry was PerKinElmerPyris 1 thermal gravimetric analyzer. Conditions and Method: the temperature was increased by 20° C./min in the range of 25 to 700° C., and the JY/T014-1996 thermal analysis method was used.

According to the present invention, the instrument for IR spectrometry was Perkin Elmer Spectrum 100 infrared spectrometer. Conditions and Method: KBr compression method, specifically comprising: grinding spectrum-pure potassium bromide into powder and drying it in an infrared oven; taking 70 mg of the spectrum-pure potassium bromide powder, compressing it into a blank potassium bromide tablet at the pressure of 20 MPa for 2 min, and scanning the background at 450 to 4000 cm$^{-1}$; grinding and thoroughly mixing about 1.5 mg of a sample together with about 200 mg of the potassium bromide powder; taking about 70 mg of the mixed powder, compressing it into a sample tablet at the pressure of 20 MPa for 2 min, and scanning the sample at 450 to 4000 cm$^{-1}$.

For any given crystal form, the relative intensity of a diffraction peak may vary due to a preferred orientation caused by factors such as the crystalline morphology, which is well known in the art of crystallography. Where a preferred orientation makes an impact, the intensity of peak is altered, but the position of the characteristic peaks of the crystal form is unchanged. In addition, there may be a small error in the peak position for any given crystal form, as also well known in the art of crystallography.

For example, the position of a peak may be shifted due to a change in temperature, movement of the sample, or instrument calibration during analysis of a sample, and the error in the measurement of 2θ values is sometimes about ±0.2 degrees. Therefore, it is well known to those skilled in the art that this error should be taken into account in determination of each crystal structure.

DSC measures the transition temperature of crystal when the crystal absorbs or releases heat due to a change in its crystalline structure or due to melting. For the same crystal form of the same compound, in a continuous analysis, the thermal transition temperature and the melting point have an error typically within about 5° C., usually within about 3° C. When it is said that a compound has a given DSC peak or melting point, it is meant that the DSC peak or melting point is within ±5° C. DSC provides an auxiliary method for distinguishing between different crystal forms. Different crystal forms may be identified according to their different characteristic transition temperatures. It is noteworthy that, for a mixture, its DSC peak or melting point may vary over a larger range. In addition, the melting temperature is associated with the elevating rate of temperature due to the decomposition occurring during melting of a material.

IR measures the infrared absorption by specific chemical bonds associated with a group in a molecule that vibrates in response to light. Because the electric environments of covalent bonds in molecules in different crystal forms are different, the strength of the covalent bonds will also have a variation which inevitably leads to a difference between the IR spectra of the different crystal forms.

In another aspect, an embodiment of the present invention provides a method for preparing crystal form A of citrate salt of the compound of Formula I, comprising the steps of:

(1) mixing the compound of Formula I, citric acid and a first solvent, optionally under heating;
(2) precipitating a solid;
(3) separating the precipitated solid;
(4) mixing the precipitated solid with a second solvent, optionally under heating; and
(5) separating the solid, and optionally drying the separated solid;

wherein, in step (1), the compound of Formula I, citric acid and the first solvent are mixed to give a solution of the compound of Formula I and citric acid;

wherein the molar ratio of compound of Formula I to citric acid is 1:0.01-100, preferably 1:0.1-10, more preferably 1:1-5, and most preferably 1:1.1;

wherein, with respect to 1 mol of the compound of Formula I, the volume of the solution obtained after mixing the compound of Formula I, citric acid and the first solvent is 0.1-100 L, preferably 1-30 L, more preferably 5-15 L, and most preferably 10 L;

the first solvent in step (1) includes, but is not limited to, one or more of water, methanol, ethanol, propanol, isopropanol, n-butanol, isobutanol, t-butanol, dichloromethane, trichloromethane, carbon tetrachloride, 1,4-dioxane, acetone, butanone, pentanone, cyclopentanone, hexanone, cyclohexanone, tetrahydrofuran, acetonitrile, benzene, toluene, xylene, N,N-dimethylformamide, N,N-dimethylacetamide or dimethyl sulfoxide, preferably one or more of methanol, ethanol, isopropanol, n-butanol, water, acetonitrile or acetone, and most preferably one or more of methanol, ethanol, water, acetonitrile, or acetone;

the mixing in step (1) may be carried out under shaking or stirring;

the duration of mixing in step (1) may be appropriately selected according to needs, and in some specific embodiments of the present invention, the duration of mixing is about 0-2 hours, preferably about 1 hour;

the heating temperature in step (1) may be from 0° C. to the boiling point of the solvent system after mixing, and in some specific embodiments of the present invention, the heating temperature is the boiling point of the solvent system after mixing;

in step (2) the state of the solid precipitated may be settled, or may be under shaking or stirring;

in step (2) the mixing may be continued after the solid is precipitated, and the duration of mixing is not particularly limited; in some specific embodiments of the present invention, the period of solid precipitation is not less than 1 hour, preferably not less than 2 hours; the mixing temperature may be from 0° C. to the boiling point of the solvent system, and in some specific embodiments of the present invention, the mixing temperature is the boiling point of the solvent system;

in step (4) the second solvent includes, but is not limited to, one or more of water, methanol, ethanol, propanol, isopropanol, n-butanol, isobutanol, t-butanol, dichloromethane, trichloromethane, carbon tetrachloride, 1,4-dioxane, acetone, butanone, pentanone, cyclopentanone, hexanone, cyclohexanone, tetrahydrofuran, acetonitrile, benzene, toluene, xylene, N,N-dimethylformamide, N,N-dimethylacetamide or dimethyl sulfoxide, preferably one or more of methanol, ethanol or water, and most preferably ethanol;

the mixing in step (4) may be carried out under shaking or stirring;

the duration of mixing in step (4) may be appropriately selected according to needs, and in some specific embodiments of the present invention, the duration of mixing is not less than 1 hour, preferably not less than 2 hours;

the heating temperature in step (4) may be from 0° C. to the boiling point of the solvent system, and in some specific embodiments of the present invention, the heating temperature is the boiling point of the solvent system;

preferably, step (1) is carried out by steps of:
  (a) adding the compound of Formula I to a third solvent to form a third solution comprising the compound of Formula I;
  (b) adding citric acid to a fourth solvent to form a fourth solution comprising citric acid; and
  (c) mixing the third and fourth solutions, optionally under heating;

wherein the volume ratio of fourth solvent to third solvent is 1:0.01-100, preferably 1:0.1-10, and most preferably 1:9;

wherein, with respect to 1 mol of the compound of Formula I, the volume of the third solution comprising the compound of Formula I is 0.1-100 L, preferably 1-30 L, more preferably 5-15 L, and most preferably 9 L;

wherein the molar concentration of citric acid in the fourth solution comprising citric acid is 0.01-100 mol/L, preferably 0.1-10 mol/L, more preferably 1-5 mol/L, and most preferably 1.1 mol/L;

the third solvent in step (a) includes, but is not limited to, one or more of water, methanol, ethanol, propanol, isopropanol, n-butanol, isobutanol, t-butanol, dichloromethane, trichloromethane, carbon tetrachloride, 1,4-dioxane, acetone, butanone, pentanone, cyclopentanone, hexanone, cyclohexanone, tetrahydrofuran, acetonitrile, benzene, toluene, xylene, N,N-dimethylformamide, N,N-dimethylacetamide or dimethyl sulfoxide, preferably one or more of methanol, ethanol, isopropanol, n-butanol or water, more preferably one or more of methanol, ethanol or water, and most preferably methanol or a mixed solvent of ethanol and water;

the fourth solvent in step (b) includes, but is not limited to, one or more of water, methanol, ethanol, propanol, isopropanol, n-butanol, isobutanol, t-butanol, dichloromethane, trichloromethane, carbon tetrachloride, 1,4-dioxane, acetone, butanone, pentanone, cyclopentanone, hexanone, cyclohexanone, tetrahydrofuran, acetonitrile, benzene, toluene, xylene, N,N-dimethylformamide, N,N-dimethylacetamide or dimethyl sulfoxide, preferably one or more of methanol, ethanol, water, acetonitrile or acetone, and most preferably methanol, ethanol, water, acetonitrile, acetone, or a mixed solvent of ethanol with water;

the mixing in step (c) may be carried out under shaking or stirring;

the duration of mixing in step (c) may be appropriately selected according to needs, and in some specific embodiments of the present invention, the duration of mixing is about 0-2 hours, preferably about 1 hour;

the heating temperature in step (c) may be from 0° C. to the boiling point of the solvent system after mixing, and in some specific embodiments of the present invention, the heating temperature is the boiling point of the solvent system after mixing.

In another aspect, an embodiment of the present invention provides a method for preparing crystal form B of citrate salt of the compound of Formula I, comprising the steps of:
  (1) mixing the compound of Formula I, citric acid and a solvent, optionally under heating;
  (2) precipitating a solid, and optionally applying heating during precipitation of the solid; and
  (3) separating the precipitated solid, and optionally drying the separated solid;

wherein, in step (1), the compound of Formula I, citric acid and the solvent are mixed to give a solution of the compound of Formula I and citric acid;

wherein the molar ratio of compound of Formula I to citric acid is 1:0.01-100, preferably 1:0.1-10, more preferably 1:1-5, and most preferably 1:1.1;

wherein, with respect to 1 mol of the compound of Formula I, the volume of the solution obtained after mixing the compound of Formula I, citric acid and the solvent is 0.1-100 L, preferably 1-30 L, more preferably 5-15 L, and most preferably 10 L;

the solvent in step (1) includes, but is not limited to, one or more of water, methanol, ethanol, propanol, isopropanol, n-butanol, isobutanol, t-butanol, dichloromethane, trichloromethane, carbon tetrachloride, 1,4-dioxane, acetone, butanone, pentanone, cyclopentanone, hexanone, cyclohexanone, tetrahydrofuran, acetonitrile, benzene, toluene, xylene, N,N-dimethylformamide, N,N-dimethylacetamide or dimethyl sulfoxide, preferably one or more of methanol, ethanol, isopropanol, n-butanol, water, acetonitrile, or acetone, and most preferably one or more of methanol, ethanol, water, acetonitrile, or acetone;

the mixing in step (1) may be carried out under shaking or stirring;

the duration of mixing in step (1) may be appropriately selected according to needs, and in some specific embodiments of the present invention, the duration of mixing is about 0-2 hours, preferably about 1 hour;

the heating temperature in step (1) may be from 0° C. to the boiling point of the solvent system after mixing, and in some specific embodiments of the present invention, the heating temperature is the boiling point of the solvent system after mixing;

in step (2), the state of the solid precipitated may be settled, or may be under shaking or stirring;

in step (2), the heating temperature may be from 0° C. to the boiling point of the solvent system, and in some specific embodiments of the present invention, the heating temperature is the boiling point of the solvent system;

preferably, step (1) is carried out by steps of:
(a) adding the compound of Formula I to a fifth solvent to form a fifth solution comprising the compound of Formula I;
(b) adding citric acid to a sixth solvent to form a sixth solution comprising citric acid; and
(c) mixing the fifth and sixth solutions, optionally under heating;

wherein the volume ratio of sixth solvent to fifth solvent is 1:0.01-100, preferably 1:0.1-50, and most preferably 1:9;

wherein, with respect to 1 mol of the compound of Formula I, the volume of the fifth solution comprising the compound of Formula I is 0.1-100 L, preferably 1-30 L, more preferably 5-15 L, and most preferably 9 L;

wherein, the molar concentration of citric acid in the sixth solution comprising citric acid is 0.01-100 mol/L, preferably 0.1-10 mol/L, more preferably 1-5 mol/L, and most preferably 1.1 mol/L;

the fifth solvent in step (a) includes, but is not limited to, one or more of water, methanol, ethanol, propanol, isopropanol, n-butanol, isobutanol, t-butanol, dichloromethane, trichloromethane, carbon tetrachloride, 1,4-dioxane, acetone, butanone, pentanone, cyclopentanone, hexanone, cyclohexanone, tetrahydrofuran, acetonitrile, benzene, toluene, xylene, N,N-dimethylformamide, N,N-dimethylacetamide or dimethyl sulfoxide, preferably one or more of methanol, ethanol, isopropanol, n-butanol or water, more preferably one or more of methanol, ethanol or water, and most preferably methanol, ethanol, a mixed solvent of methanol and water, or a mixed solvent of ethanol and water;

the sixth solvent in step (b) includes, but is not limited to, one or more of water, methanol, ethanol, propanol, isopropanol, n-butanol, isobutanol, t-butanol, dichloromethane, trichloromethane, carbon tetrachloride, 1,4-dioxane, acetone, butanone, pentanone, cyclopentanone, hexanone, cyclohexanone, tetrahydrofuran, acetonitrile, benzene, toluene, xylene, N,N-dimethylformamide, N,N-dimethylacetamide or dimethyl sulfoxide, preferably one or more of methanol, ethanol or water, and most preferably water, a mixed solvent of methanol and water, or a mixed solvent of ethanol and water;

the mixing in step (c) may be carried out under shaking or stirring;

the duration of mixing in step (c) may be appropriately selected according to needs, and in some specific embodiments of the present invention, the duration of mixing is about 0-2 hours, preferably about 1 hour;

the heating temperature in step (c) may be from 0° C. to the boiling point of the solvent system after mixing, and in some specific embodiments of the present invention, the heating temperature is the boiling point of the solvent system after mixing.

In yet another aspect, an embodiment of the present invention provides a method for preparing crystal form C of citrate salt of the compound of Formula I, comprising the steps of:
(1) mixing the compound of Formula I, citric acid and a seventh solvent, optionally under heating;
(2) precipitating a solid;
(3) separating the precipitated solid;
(4) mixing the precipitated solid with an eighth solvent, optionally under heating; and
(5) separating the solid, and optionally drying the separated solid;

wherein, in step (1), the compound of Formula I, citric acid and the seventh solvent are mixed to give a solution of the compound of Formula I and citric acid;

wherein the molar ratio of compound of Formula I to citric acid is 1:0.01-100, preferably 1:0.1-10, more preferably 1:1-5, and most preferably 1:1.1;

wherein, with respect to 1 mol of the compound of Formula I, the volume of the solution obtained after mixing the compound of Formula I, citric acid and the seventh solvent is 0.1-100 L, preferably 1-30 L, more preferably 5-15 L, and most preferably 10 L;

the seventh solvent in step (1) includes, but is not limited to, one or more of water, methanol, ethanol, propanol, isopropanol, n-butanol, isobutanol, t-butanol, dichloromethane, trichloromethane, carbon tetrachloride, 1,4-dioxane, acetone, butanone, pentanone, cyclopentanone, hexanone, cyclohexanone, tetrahydrofuran, acetonitrile, benzene, toluene, xylene, N,N-dimethylformamide, N,N-dimethylacetamide or dimethyl sulfoxide, preferably one or more of methanol, ethanol, isopropanol, n-butanol, water, acetonitrile, or acetone, and most preferably one or more of methanol, ethanol, or water;

the mixing in step (1) may be carried out under shaking or stirring;

the duration of mixing in step (1) may be appropriately selected according to needs, and in some specific embodiments of the present invention, the duration of mixing is about 0 to 2 hours, preferably about 0.5 to 1.5 hours, and most preferably about 1 hour;

the heating temperature in step (1) may be from 0° C. to the boiling point of the solvent system after mixing, and in some specific embodiments of the present invention, the heating temperature is the boiling point of the solvent system after mixing;

in step (2) the state of the solid precipitated may be settled, or may be under shaking or stirring;

in step (4) the eighth solvent includes, but is not limited to, one or more of water, methanol, ethanol, propanol, isopropanol, n-butanol, isobutanol, t-butanol, dichloromethane, trichloromethane, carbon tetrachloride, 1,4-dioxane, acetone, butanone, pentanone, cyclopentanone, hexanone, cyclohexanone, tetrahydrofuran, acetonitrile, benzene, toluene, xylene, N,N-dimethylformamide, N,N-dimethylacetamide or dimethyl sulfoxide, preferably one or more of methanol, ethanol or water, and most preferably ethanol;

the mixing in step (4) may be carried out under shaking or stirring;

the duration of mixing in step (4) may be appropriately selected according to needs, and in some specific embodiments of the present invention, the duration of mixing is about 0 to 2 hours, preferably about 1 hour;

the heating temperature in step (4) may be from 0° C. to the boiling point of the solvent system, and in some specific embodiments of the present invention, the heating temperature is the boiling point of the solvent system;

preferably, step (1) is carried out by steps of:
(a) adding the compound of Formula I to a ninth solvent to form a ninth solution comprising the compound of Formula I;
(b) adding citric acid to a tenth solvent to form a tenth solution comprising citric acid; and
(c) mixing the ninth and tenth solutions, optionally under heating;

wherein the volume ratio of tenth solvent to ninth solvent is 1:0.01-100, preferably 1:0.1-50, and most preferably 1:9;

wherein, with respect to 1 mol of the compound of Formula I, the volume of the ninth solution comprising the compound of Formula I is 0.1-100 L, preferably 1-30 L, more preferably 5-15 L, and most preferably 9 L;

wherein the molar concentration of citric acid in the tenth solution comprising citric acid is 0.01-100 mol/L, preferably 0.1-10 mol/L, more preferably 1-5 mol/L, and most preferably 1.1 mol/L;

the ninth solvent in step (a) includes, but is not limited to, one or more of water, methanol, ethanol, propanol, isopropanol, n-butanol, isobutanol, t-butanol, dichloromethane, trichloromethane, carbon tetrachloride, 1,4-dioxane, acetone, butanone, pentanone, cyclopentanone, hexanone, cyclohexanone, tetrahydrofuran, acetonitrile, benzene, toluene, xylene, N,N-dimethylformamide, N,N-dimethylacetamide or dimethyl sulfoxide, preferably one or more of methanol, ethanol, isopropanol, n-butanol or water, more preferably one or more of methanol, ethanol or water, and most preferably methanol, ethanol, a mixed solvent of methanol and water, or a mixed solvent of ethanol and water;

the tenth solvent in step (b) includes, but is not limited to, one or more of water, methanol, ethanol, propanol, isopropanol, n-butanol, isobutanol, t-butanol, dichloromethane, trichloromethane, carbon tetrachloride, 1,4-dioxane, acetone, butanone, pentanone, cyclopentanone, hexanone, cyclohexanone, tetrahydrofuran, acetonitrile, benzene, toluene, xylene, N,N-dimethylformamide, N,N-dimethylacetamide or dimethyl sulfoxide, preferably one or more of methanol, ethanol, or water, and most preferably water, a mixed solvent of methanol and water, or a mixed solvent of ethanol and water;

the mixing in step (c) may be carried out under shaking or stirring;

the duration of mixing in step (c) may be appropriately selected according to needs, and in some specific embodiments of the present invention, the duration of mixing is about 0-2 hours, preferably about 1 hour;

the heating temperature in step (c) may be from 0° C. to the boiling point of the solvent system after mixing, and in some specific embodiments of the present invention, the heating temperature is the boiling point of the solvent system after mixing.

In another aspect, an embodiment of the present invention provides a crystalline composition comprising a crystal of citrate salt of the compound of Formula I, wherein the crystal of citrate salt of the compound of Formula I accounts for 50% or more, preferably 80% or more, more preferably 90% or more, and most preferably 95% or more by weight of the crystalline composition; wherein the crystal of citrate salt of the compound of Formula I is crystal form A, crystal form B, or crystal form C of citrate salt of the compound of Formula I.

In yet another aspect, an embodiment of the present invention provides a pharmaceutical composition comprising a crystal of citrate salt of the compound of Formula I or a crystalline composition comprising the crystal, the pharmaceutical composition comprises a therapeutically effective amount of a crystal of citrate salt of the compound of Formula I or a crystalline composition comprising the crystal, wherein the crystal of citrate salt of the compound of Formula I is crystal form A of citrate salt of the compound of Formula I, crystal form B of citrate salt of the compound of Formula I, or crystal form C of citrate salt of the compound of Formula I. The pharmaceutical composition according to the present invention may or may not contain pharmaceutically acceptable auxilliaries. In addition, the pharmaceutical composition according to the present invention may further include one or more other therapeutic agents.

The "pharmaceutically acceptable auxilliaries" refer to inert substances which are administered together with active ingredients to facilitate administration of the active ingredients, including, but not limited to, any glidants, sweeteners, diluents, preservatives, dyes/colorants, flavor enhancers, surfactants, wetting agents, dispersing agents, disintegrants, suspending agents, stabilizers, isotonizing agents, solvents or emulsifiers acceptable for human or animal use (eg, domestic animals) as approved by the China Food and Drug Administration. Non-limiting examples of such auxilliaries include calcium carbonate, calcium phosphate, various sugars and various types of starch, cellulose derivatives, gelatin, vegetable oils, and polyethylene glycol.

The pharmaceutical compositions according to the present invention may be formulated into a solid, semi-solid, liquid or gaseous formulation, such as a tablet, a pill, a capsule, powder, granules, an ointment, an emulsion, a suspension, a solution, a suppository, an injection, an inhalant, gel, microspheres, aerosol, and the like.

Typical administration routes for the pharmaceutical composition according to the present invention include, but are not limited to, oral, rectal, transmucosal, enteral, or topical, transdermal, inhalational, parenteral, sublingual, intravaginal, intranasal, intraocular, intraperitoneal, intramuscular, subcutaneous, or intravenous administration. The preferred administration route is oral administration.

In a further aspect, an embodiment of the present invention provides a method for modulating the activity of a protein kinase, comprising contacting the protein kinase with a crystal of citrate salt of the compound of Formula I, wherein the crystal of citrate salt of the compound of Formula I is crystal form A of citrate salt of the compound of Formula I, crystal form B of citrate salt of the compound of Formula I, or crystal form C of citrate salt of the compound of Formula I. Preferably, the protein kinase is selected from ALK. In addition, the protein kinase includes mutated kinases, which are selected from mutated ALK kinases.

In a further aspect, an embodiment of the present invention provides a use of a crystal of citrate salt of the compound of Formula I, or a crystalline composition comprising the crystal, or a pharmaceutical composition comprising the crystal, or a pharmaceutical composition comprising the crystalline composition, in the manufacture of a medicament for treatment and/or prophylaxis of a disease, wherein the crystal of citrate salt of the compound of Formula I is crystal form A of citrate salt of the compound of Formula I, crystal form B of citrate salt of the compound of Formula I, or crystal form C of citrate salt of the compound of Formula I, wherein the disease is a disease associated with activity of protein kinases (e.g, ALK), for example, abnormal cell proliferation, wherein the abnormal cell proliferation includes cancers.

An embodiment of the present invention further provides a use of a crystal of citrate salt of the compound of Formula I, or a crystalline composition comprising the crystal, or a pharmaceutical composition comprising the crystal, or a pharmaceutical composition of the crystalline composition, in the manufacture of a medicament for treatment and/or prophylaxis of an ALK-mediated disease, wherein the crystal of citrate salt of the compound of Formula I is crystal form A of citrate salt of the compound of Formula I, crystal form B of citrate salt of the compound of Formula I, or crystal form C of citrate salt of the compound of Formula I.

The ALK-mediated disease includes ALK-positive non-small cell lung cancer, anaplastic large-cell lymphoma, inflammatory myofibroblastic tumor, nasopharyngeal carcinoma, breast cancer, colorectal cancer, diffuse large B-cell lymphoma, systemic histiocytosis, neuroblastoma and the like, preferably includes ALK-positive non-small cell lung cancer, and more preferably includes ALK-positive primary or metastatic non-small cell lung cancer.

Additionally, an embodiment of the present invention further provides a method for treating and/or prophylaxing a disease associated with activity of a protein kinase (e.g. ALK) in a mammal (e.g. human), comprising administering to the mammal (e.g. human) a therapeutically effective amount of a crystal of citrate salt of the compound of Formula I, or a crystalline composition comprising the crystal, or a pharmaceutical composition comprising the crystal, or a pharmaceutical composition comprising the crystalline composition, wherein the crystal of citrate salt of the compound of Formula I is crystal form A of citrate salt of the compound of Formula I, crystal form B of citrate salt of the compound of Formula I, or crystal form C of citrate salt of the compound of Formula I.

Furthermore, an embodiment of the present invention further provides a crystal of citrate salt of the compound of Formula I, or a crystalline composition comprising the crystal, or a pharmaceutical composition comprising the crystal, or a pharmaceutical composition comprising the crystalline composition, for use in modulating activity of protein kinase(s) or for use in treating and/or prophylaxing a disease associated with activity of a protein kinase in a mammal (e.g. human), wherein the crystal of citrate salt of the compound of Formula I is crystal form A of citrate salt of the compound of Formula I, crystal form B of citrate salt of the compound of Formula I, or crystal form C of citrate salt of the compound of Formula I. Preferably, the protein kinase is ALK.

In addition, the protein kinase includes mutated kinases, which are selected from mutated ALKs.

DETAILED DESCRIPTION OF INVENTION

Figure 1:
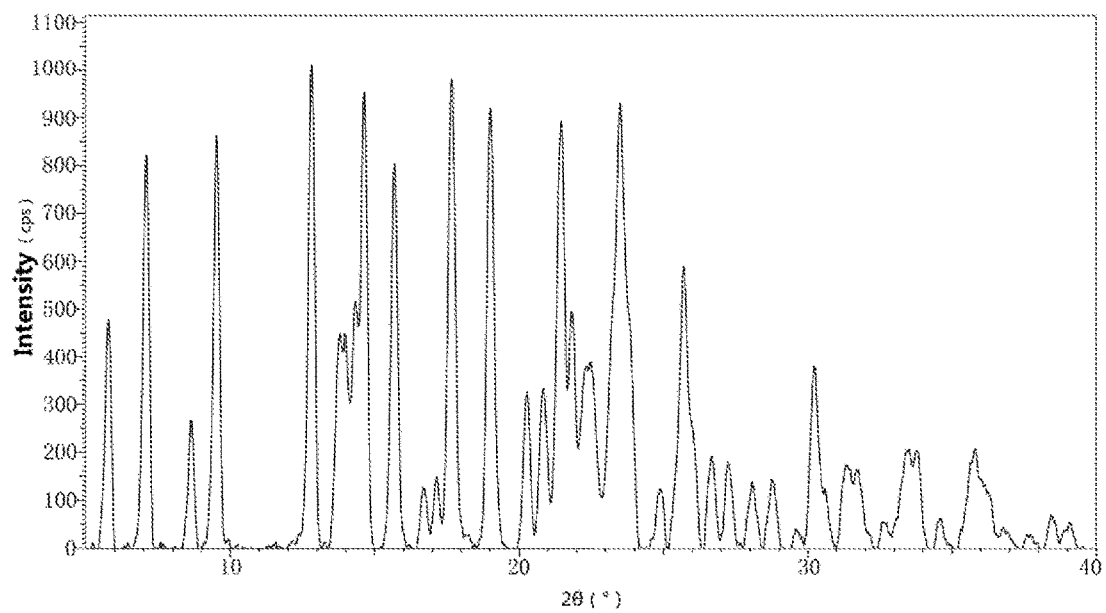
FIG. 1 is an XRD pattern of crystal form A of citrate salt of the compound of Formula I prepared in Example 2.

The technical solutions of the present invention will be described in detail below with reference to the accompanying drawings and Examples. However, the scope of protection of the present invention includes but not limited thereto.

Example 1 Preparation of the Compound of Formula I

Preparation of Intermediate 1

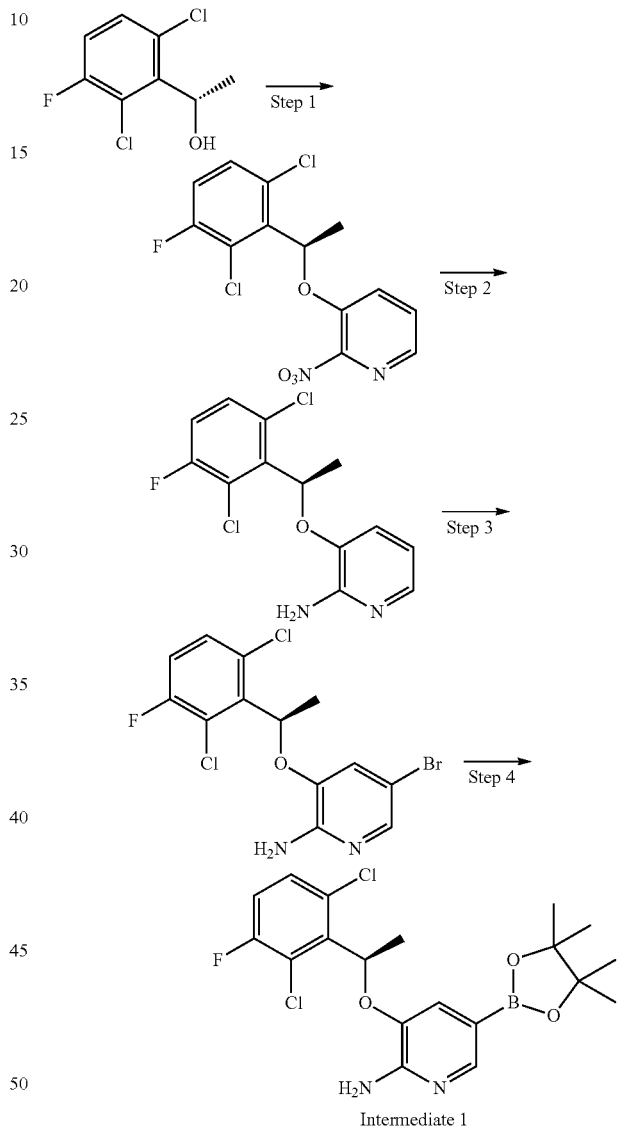

Intermediate 1

Step 1:

(S)-1-(2,6-dichloro-3-fluorophenyl)ethanol (20.9 g, 0.10 mol) was dissolved in 200 mL anhydrous tetrahydofuran, to which 3-hydroxy-2-nitropyridine (16.0 g, 0.11 mol) and triphenylphosphine (40.0 g, 0.15 mol) were sequentially added under a nitrogen atmosphere, and the reaction solution was stirred at room temperature for 1 hour, cooled to 0° C. and diisopropyl azodicarboxylate (40 mL, 0.15 mol) was added dropwise. After the addition was complete, stirring was continued at 0° C. for 12 hours. The solvent was distilled off to obtain an oily material, which was separated by silica gel column chromatography, to give (R)-3-(1-(2, 6-dichloro-3-fluorophenyl)ethoxy)-2-nitropyridine (20.2 g). Yield: 61%.

Step 2:

At 0° C. and under stirring, to a solution of (R)-3-(1-(2,6-dichloro-3-fluorophenyl)ethoxy)-2-nitropyridine (20.0 g, 60 mmol) in ethanol (300 mL), 15 mL of 2 M hydrochloric acid and reduced iron powder (27 g, 480 mmol) were added, followed by refluxing for 12 hours. After cooling to room temperature and filtration, the filtrate was concentrated to give (R)-3-(1-(2,6-dichloro-3-fluorophenyl)ethoxy)-2-aminopyridine (17.0 g), which was directly used for the next step. Yield: 94%. MS m/z[ESI]: 301.0[M+1].

Step 3:

At 0° C. and under stirring, to a solution of (R)-3-(1-(2,6-dichloro-3-fluorophenyl)ethoxy)-2-aminopyridine (15.0 g, 50 mmol) in acetonitrile (200 mL), bromosuccinimide (10 g, 56 mmol) was added in batches, followed by a reaction at 0° C. for 1 hour. Subsequently, the solvent was distilled off, and dichloromethane was added. The organic phase was washed with a saturated sodium bicarbonate solution and dried over anhydrous sodium sulfate. After concentration under reduced pressure, the residue was separated by silica gel column chromatography, to give (R)-3-(1-(2,6-dichloro-3-fluorophenyl)ethoxy)-5-bromo-2-aminopyridine (9.88 g). Yield: 52%. MS m/z[ESI]: 380.9[M+1].

Step 4:

(R)-3-(1-(2,6-dichloro-3-fluorophenyl)ethoxy)-5-bromo-2-aminopyridine (7.6 g, 20 mmol), bis(pinacolato)diboron (7.56 g, 30 mmol), Pd(dppf)Cl$_2$ (732 mg, 1 mmol) and anhydrous potassium acetate (4.90 g, 50 mmol) were added to dry dioxane (200 mL), purged with nitrogen and allowed to react at 100° C. for 4 hours. After cooling, the solvent was distilled off under reduced pressure, and the residue was separated by silica gel column chromatography, to give (R)-3-(1-(2,6-dichloro-3-fluorophenyl) ethoxy)-5-(4,4,5,5-tetramethyl-1,3,2-dioxaborolan-2-yl)-2-aminopyridine (5.46 g). Yield: 64%. MS m/z[ESI]: 427.1[M+1].

Preparation of Intermediate 2

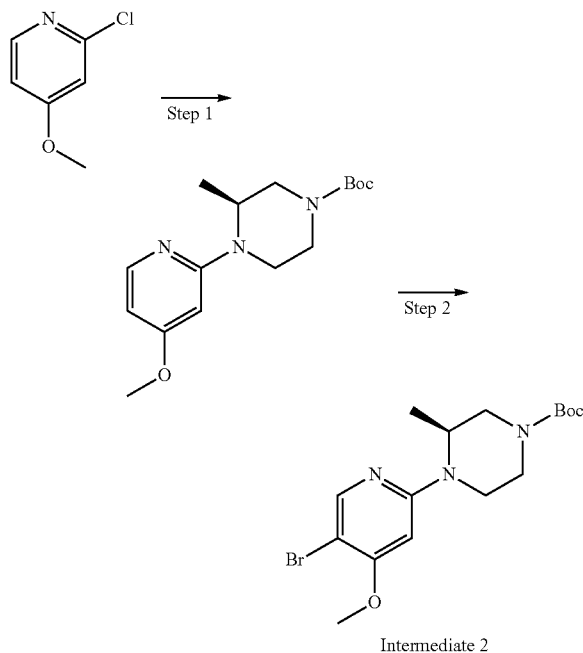

Intermediate 2

Step 1:

2-chloro-4-methoxypyridine (2.58 g, 18 mmol), (S)-3-methyl-1-tert-butoxycarbonylpiperazine (5.4 g, 27 mmol), Pd$_2$(dba)$_3$ (824 mg, 0.9 mmol), 2,2'-bis(diphenylphosphino)-1,1'-binaphthyl (1.12 g, 1.8 mmol) and potassium tert-butoxide (5.01 g, 45 mmol) were added to dry toluene (200 mL), and refluxed for 16 hours under a nitrogen atmosphere. Subsequently, the reaction solution was cooled to room temperature, filtrated and concentrated under reduced pressure. The residue was separated by silica gel column chromatography, to give the target compound. Yield: 50%. MS m/z[ESI]: 308.2[M+1].

Step 2:

At 0° C. and under stirring, to a solution of tert-butyl (S)-4-(4-methoxypyridin-2-yl)-3-methylpiperazine-1-carboxylate (2.46 g, 8 mmol) in acetonitrile (50 mL), bromosuccinimide (1.57 g, 8.8 mmol) was added in batches, followed by a reaction at room temperature for 2 hours. The solvent was distilled off at reduced pressure, and dichloromethane was added. The organic phase was washed with a saturated sodium bicarbonate solution and dried over anhydrous sodium sulfate. After concentration under reduced pressure, the residue was separated by silica gel column chromatography to give Intermediate 2. Yield: 75%. MS m/z[ESI]: 386.1 [M+1].

Preparation of the Compound of Formula I

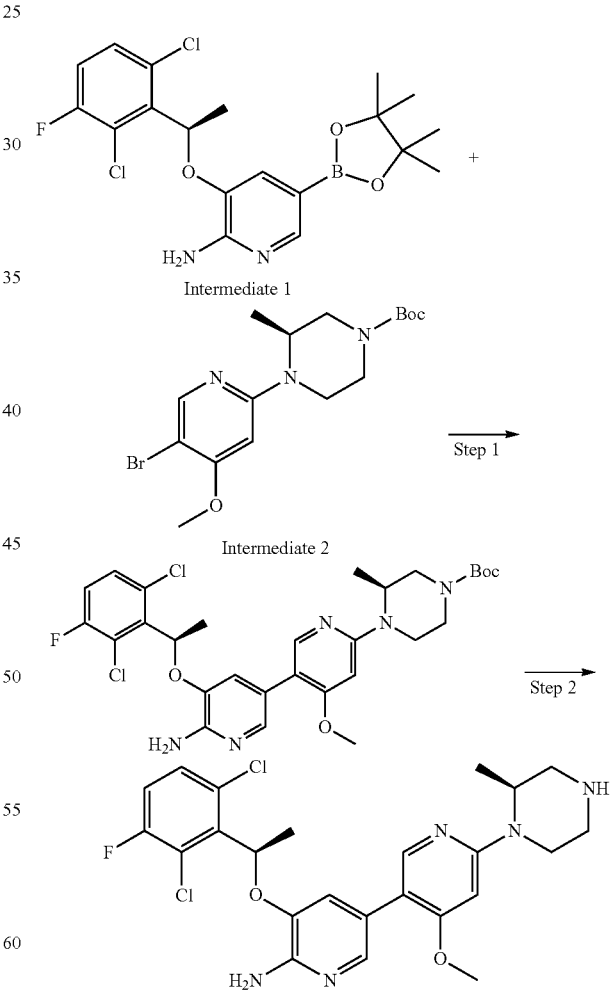

Step 1:

Tert-butyl (S)-4-(5-bromo-4-methoxypyridin-2-yl)-3-methylpiperazine-1-carboxylate (106 mg, 0.275 mmol), (R)-3-(1-(2,6-dichloro-3-fluorophenyl)ethoxy)-5-(4,4,5,5-tetramethyl-1,3,2-dioxaborolan-2-yl)-2-aminopyridine (140 mg, 0.33 mmol), Tetrakis(Triphenylphosphine)Palladium (32 mg, 0.0275 mmol) and cesium carbonate (179 mg, 0.55 mmol) were added to dioxane (10 mL) and water (1.5 mL), purged with nitrogen and allowed to react at 100° C. overnight. After cooling, the residue was separated by silica gel column chromatography, to give 5-((R)-1-(2,6-dichloro-3-fluorophenyl)ethoxy)-4'-methoxy-6'-((S)-2-methyl-4-tert-butoxycarbonylpiperazine-1-yl)-3,3'-bipyridine-6-amine (70 mg). Yield: 42%. MS m/z[ESI]: 606.2[M+1].

Step 2:

Under stirring, trifluoroacetic acid (1 mL) was added to a solution of 5-((R)-1-(2,6-dichloro-3-fluorophenyl)ethoxy)-4'-methoxy-6'-((S)-2-methyl-4-tert-but oxycarbonylpiperazine-1-yl)-3,3'-bipyridine-6-amine (67 mg, 0.11 mmol) in dichloromethane (10 mL), and stirred for 1 hour. Subsequently, the reaction mixture was adjusted to a pH greater than 13 with a 10 mol/L aqueous sodium hydroxide solution, and then extracted with dichloromethane. The organic phase was dried over anhydrous sodium sulfate and filtrated. The filtrate was concentrated and purified by silica gel column chromatography (eluent: dichloromethane:methanol=8:1), to give 5-((R)-1-(2,6-dichloro-3-fluorophenyl)ethoxy)-4'-methoxy-6'-((S)-2-methylpiperazin-1-yl)-3,3'-bipyridin-6-amine (30 mg). Yield: 55%.

MS m/z [ESI]: 506.1[M+1];

$^1$H-NMR (400 MHz, CDCl$_3$): δ=7.94 (1H, s), 7.71 (1H, s), 7.28-7.32 (1H, m), 7.07 (1H, t, J=8.4 Hz), 6.97 (1H, s), 6.04-6.13 (2H, m), 4.86 (2H, s), 4.57-4.59 (1H, m), 4.03 (1H, d, J=14 Hz), 3.76 (3H, s), 3.07-3.33 (4H, m), 2.88-3.00 (1H, m), 1.84 (3H, d, J=6.8 Hz), 1.34 (3H, d, J=6.8 Hz).

Example 2 Preparation of Crystal Form A of Citrate Salt of Compound of Formula I 0.01 mol of the compound of Formula I was dissolved in 90 mL methanol, and a prepared 10 mL of 1.1 mol/L citric acid solution in methanol was added thereto under refluxing and stirring. After a 1-hour reaction, a solid was precipitated from the reaction mixture, and the refluxing was continued for 1-2 hours. After filtration, the separated solid was refluxed and stirred in ethanol for 2-3 hours, and filtrated. The separated solid was air-blown dried at 85° C. under ambient pressure, to give crystal form A of citrate salt of the compound of Formula I. mp: 205.1 to 206.4° C. (using a BUCHI melting point instrument B-545, heating rate: 10° C./min).

Figure 4:
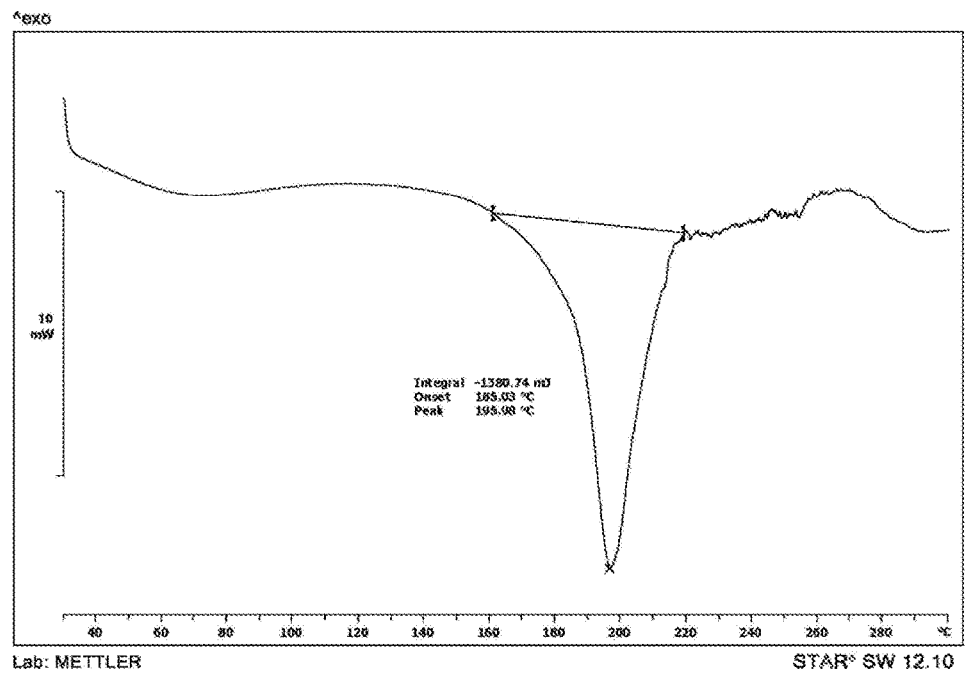
FIG. 4 is a DSC curve of crystal form A of citrate salt of the compound of Formula I prepared in Example 2.
Figure 7:
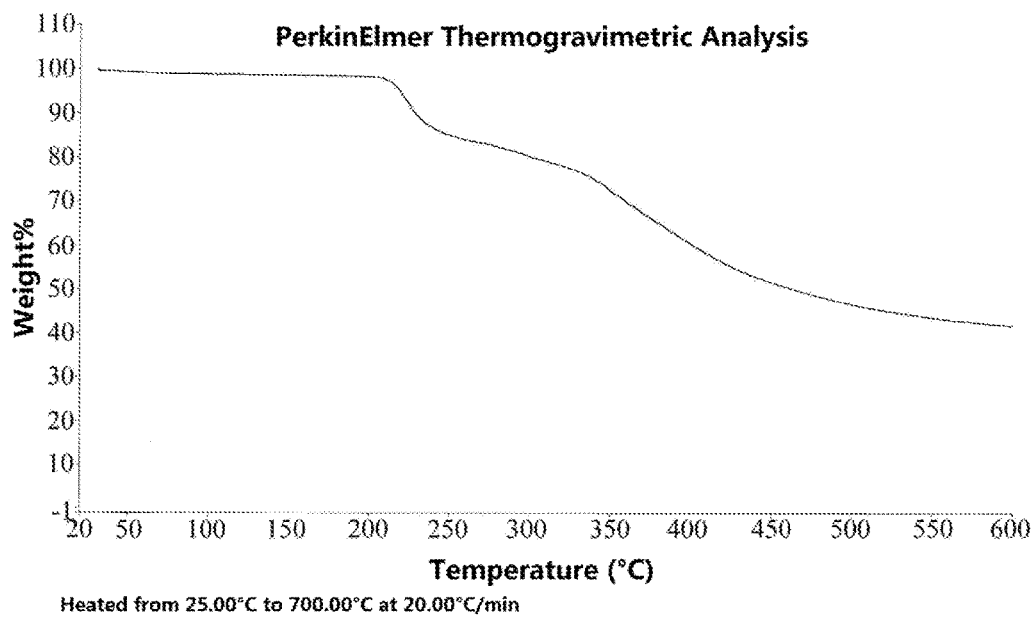
FIG. 7 is a thermogravimetric analysis (TGA) curve of crystal form A of citrate salt of the compound of Formula I prepared in Example 2.
Figure 9:
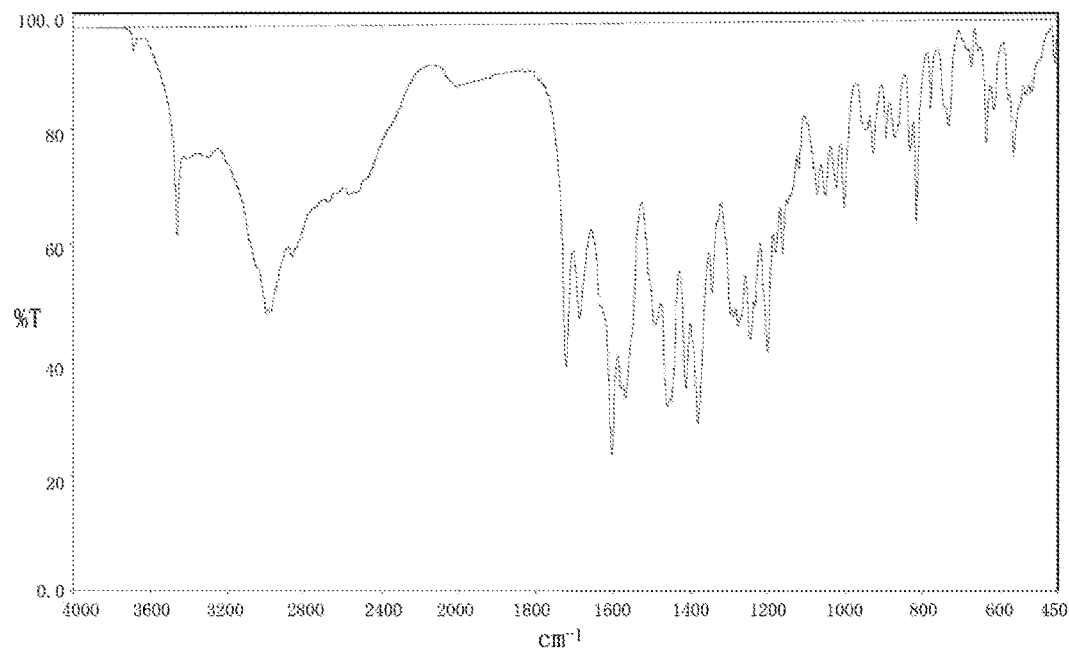
FIG. 9 is an infrared absorption spectrum (IR) of crystal form A of citrate salt of the compound of Formula I prepared in Example 2.

An X-ray powder diffraction pattern thereof with Cu Kα radiation is shown in FIG. 1, a differential scanning calorimetry (DSC) curve is shown in FIG. 4, a thermogravimetric analysis (TGA) curve is shown in FIG. 7, and an infrared absorption spectrum (IR) is shown in FIG. 9.

Example 3 Preparation of Crystal Form A of Citrate Salt of Compound of Formula I 0.01 mol of the compound of Formula I was dissolved in 90 mL methanol, and a prepared 10 mL of 1.1 mol/L citric acid solution in ethanol was added thereto under refluxing and stirring. After a 1-hour reaction, a solid was precipitated from the reaction mixture, and the refluxing was continued for 1-2 hours. After filtration, the separated solid was refluxed and stirred in ethanol for 2-3 hours, and filtrated. The separated solid was air-blown dried at 85° C. under ambient pressure, to give crystal form A of citrate salt of the compound of Formula I.

Example 4 Preparation of Crystal Form A of Citrate Salt of Compound of Formula I 0.01 mol of the compound of Formula I was dissolved in 90 mL methanol, and a prepared 10 mL of 1.1 mol/L citric acid solution in water was added thereto under refluxing and stirring. After a 1-hour reaction, a solid was precipitated from the reaction mixture, and the refluxing was continued for 1-2 hours. After filtration, the separated solid was refluxed and stirred in ethanol for 2-3 hours, and filtrated. The separated solid was air-blown dried at 85° C. under ambient pressure, to give crystal form A of citrate salt of the compound of Formula I.

Example 5 Preparation of Crystal Form A of Citrate Salt of Compound of Formula I 0.01 mol of the compound of Formula I was dissolved in 90 mL methanol, and a prepared 10 mL of 1.1 mol/L citric acid solution in acetonitrile was added thereto under refluxing and stirring. After a 1-hour reaction, a solid was precipitated from the reaction mixture, and the refluxing was continued for 1-2 hours. After filtration, the separated solid was refluxed and stirred in ethanol for 2-3 hours, and filtrated. The separated solid was air-blown dried at 85° C. under ambient pressure, to give crystal form A of citrate salt of the compound of Formula I.

Example 6 Preparation of Crystal Form A of Citrate Salt of Compound of Formula I 0.01 mol of the compound of Formula I was dissolved in 90 mL methanol, and a prepared 10 mL of 1.1 mol/L citric acid solution in acetone was added under refluxing and stirring. After a 1-hour reaction, a solid was precipitated from the reaction mixture, and the refluxing was continued for 1-2 hours. After filtration, the separated solid was refluxed and stirred in ethanol for 2-3 hours, and filtrated. The separated solid was air-blown dried at 85° C. under ambient pressure, to give crystal form A of citrate salt of the compound of Formula I.

Example 7 Preparation of Crystal Form A of Citrate Salt of Compound of Formula I 0.01 mol of the compound of Formula I was dissolved in 90 mL of a mixed solvent of ethanol/water (the volume ratio of ethanol to water is 95:5), and a prepared 10 mL of 1.1 mol/L citric acid solution in ethanol/water (the volume ratio of ethanol to water is 95:5) was added thereto under refluxing and stirring. After a 1-hour reaction, a solid was precipitated from the reaction mixture. After filtration, the separated solid was refluxed and stirred in ethanol for 2-3 hours, and filtrated. The separated solid was air-blown dried at 85° C. under ambient pressure, to give crystal form A of citrate salt of the compound of Formula I.

Example 8 Preparation of Crystal Form B of Citrate Salt of Compound of Formula I 0.01 mol of the compound of Formula I was dissolved in 90 mL of a mixed solvent of ethanol/water (the volume ratio of ethanol to water is 95:5), and a prepared 10 mL of 1.1 mol/L citric acid solution in ethanol/water (the volume ratio of ethanol to water is 95:5) was added thereto under refluxing and stirring. After a 1-hour reaction, a solid was precipitated from the reaction mixture. After filtration, the separated solid was air-blown dried at 85° C. under ambient pressure, to give crystal form B of citrate salt of the compound of Formula I. mp: 200.6-202.6° C. (using a BUCHI melting point instrument B-545, heating rate: 10° C./min).

Figure 2:
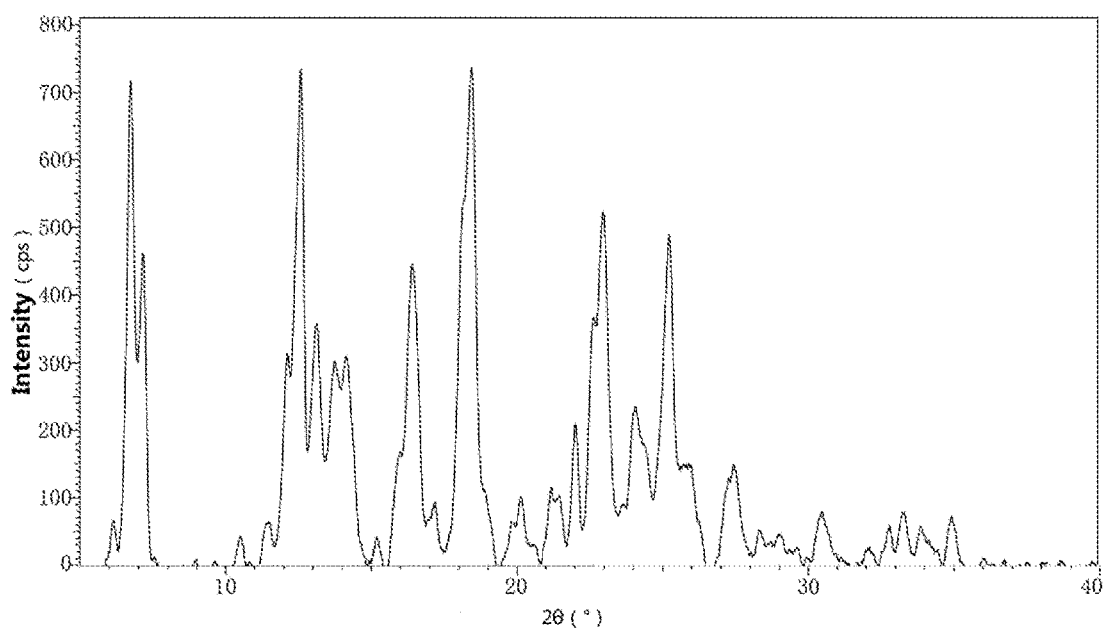
FIG. 2 is an XRD pattern of crystal form B of citrate salt the compound of Formula I prepared in Example 8.
Figure 5:
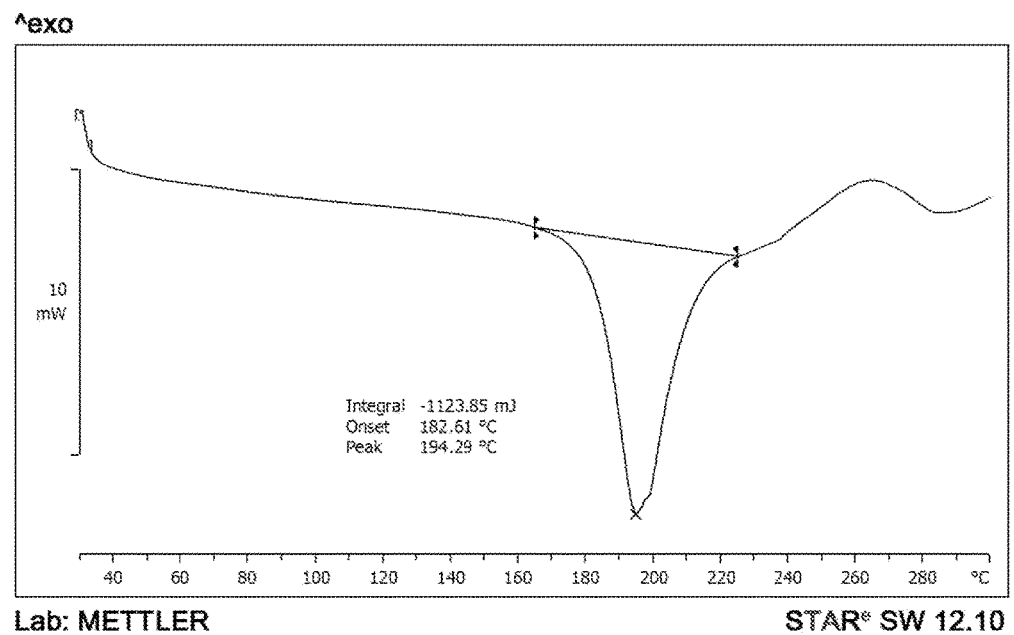
FIG. 5 is a DSC curve of crystal form B of citrate salt of the compound of Formula I prepared in Example 8.
Figure 8:
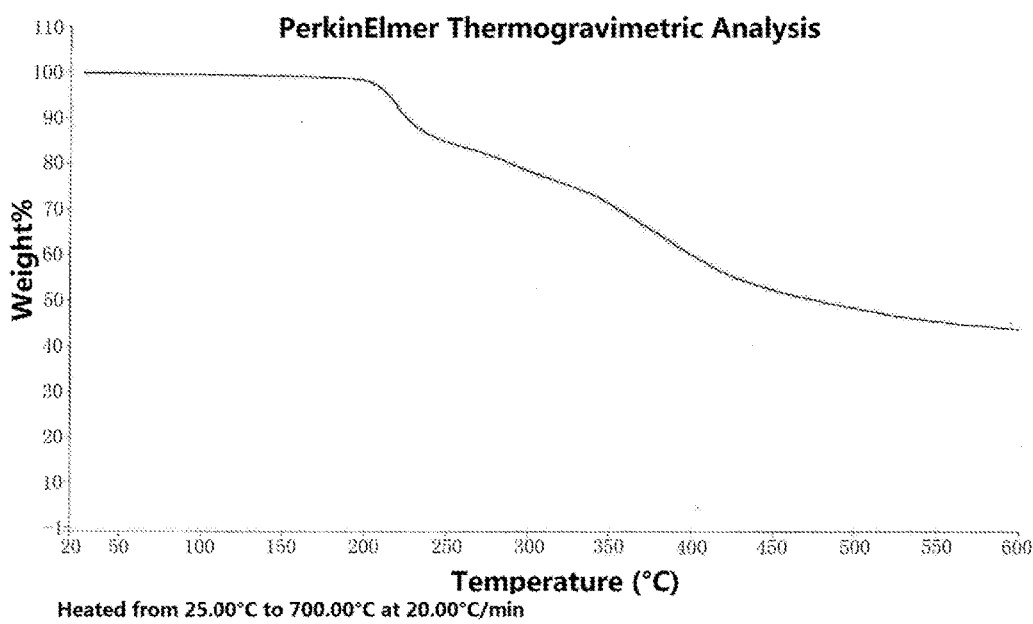
FIG. 8 is a thermogravimetric analysis (TGA) curve of crystal form B of citrate salt of the compound of Formula I prepared in Example 8.
Figure 10:
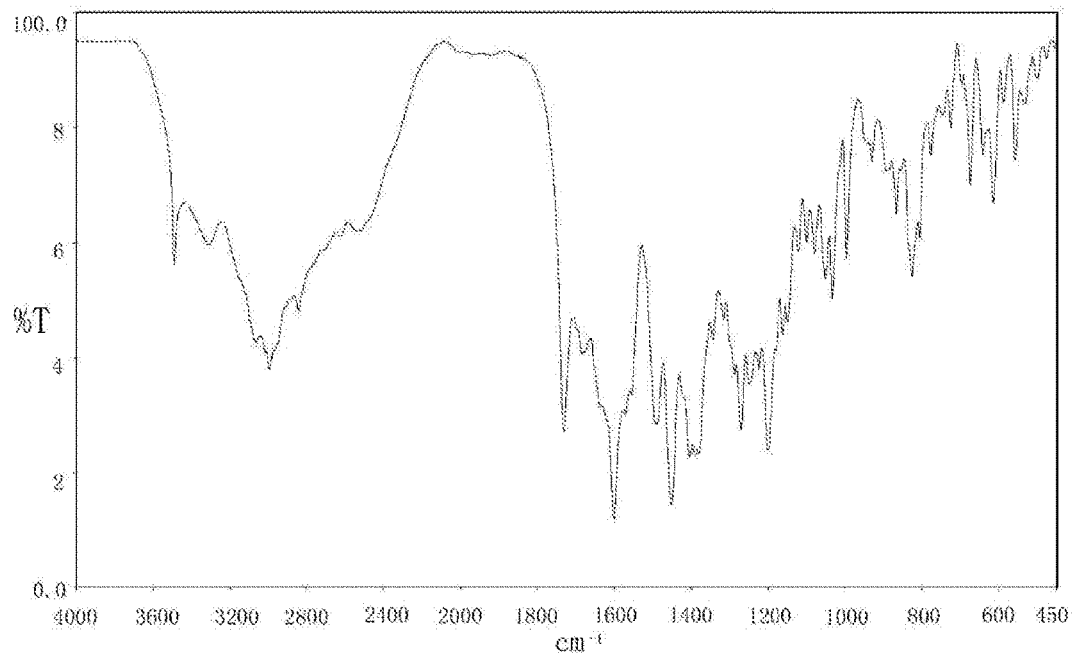
FIG. 10 is an infrared absorption spectrum (IR) of crystal form B of citrate salt of the compound of Formula I prepared in Example 8.

An X-ray powder diffraction pattern thereof with Cu Kα radiation is shown in FIG. 2, a differential scanning calorimetry (DSC) curve is shown in FIG. 5, a thermogravimetric analysis (TGA) curve is shown in FIG. 8, and an infrared absorption spectrum (IR) is shown in FIG. 10.

Example 9 Preparation of Crystal Form B of Citrate Salt of Compound of Formula I 0.01 mol of the compound of Formula I was dissolved in 90 mL anhydrous ethanol, and a prepared 10 mL of 1.1 mol/L citric acid solution in water was added thereto under refluxing and stirring. After a 1-hour reaction, a solid was precipitated from the reaction mixture. After filtration, the separated solid was air-blown dried at 85° C. under ambient pressure, to give crystal form B of citrate salt of the compound of Formula I.

Example 10 Preparation of Crystal Form B of Citrate Salt of Compound of Formula I 0.01 mol of the compound of Formula I was dissolved in 90 mL of a mixed solvent of methanol/water (the volume ratio of methanol to water is 95:5), and a prepared 10 mL of 1.1 mol/L citric acid solution in methanol/water (the volume ratio of methanol to water is 95:5) was added thereto under refluxing and stirring. After a 1-hour reaction, a solid was precipitated from the reaction mixture. After filtration, the separated solid was air-blown dried at 85° C. under ambient pressure, to give crystal form B of citrate salt of the compound of Formula I.

Example 11 Preparation of Crystal Form B of Citrate Salt of Compound of Formula I 0.01 mol of the compound of Formula I was dissolved in 90 mL methanol, and a prepared 10 mL of 1.1 mol/L citric acid solution in water was added thereto under refluxing and stirring. After a 1-hour reaction, a solid was precipitated from the reaction mixture. After filtration, the separated solid was air-blown dried at 85° C. under ambient pressure, to give crystal form B of citrate salt of the compound of Formula I.

Example 12 Preparation of Crystal Form C of Citrate Salt of Compound of Formula I 0.01 mol of the compound of Formula I was dissolved in 90 mL of a mixed solvent of ethanol/water (the volume ratio of ethanol to water is 95:5), and a prepared 10 mL of 1.1 mol/L citric acid solution in ethanol/water (the volume ratio of ethanol to water is 95:5) was added thereto under refluxing and stirring. After a 1-hour reaction, a solid was precipitated from the reaction mixture. After filtration, the separated solid was refluxed and stirred in ethanol for 1 hour, and filtrated. The separated solid was air-blown dried at 85° C. under ambient pressure, to give crystal form C of citrate salt of the compound of Formula I. mp: 201.3-203.5 (using a BUCHI melting point instrument B-545, heating rate: 10° C./min).

Figure 3:
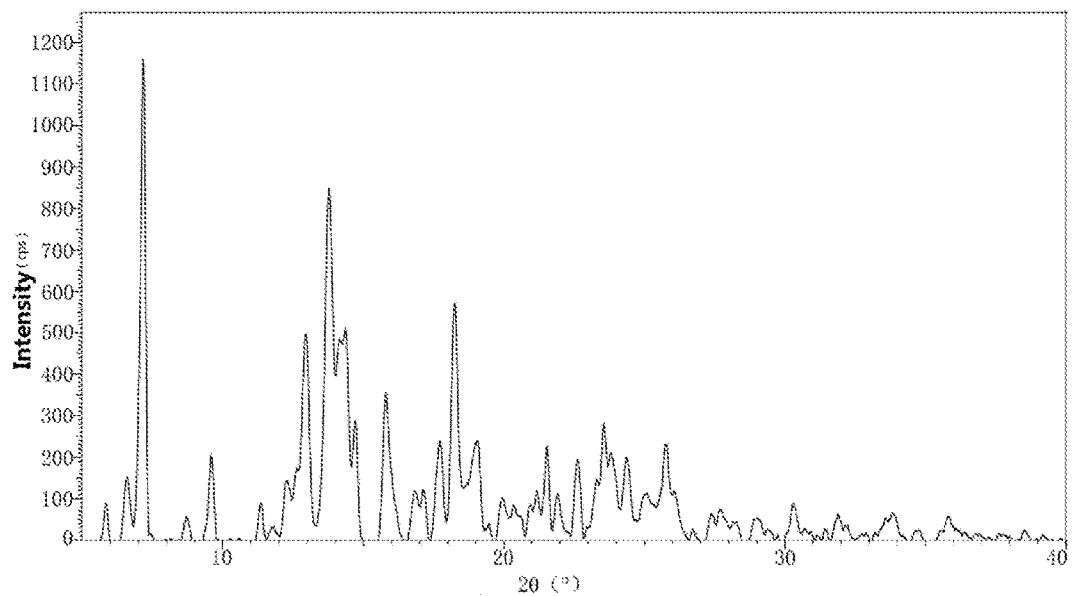
FIG. 3 is an XRD pattern of crystal form C of citrate salt of the compound of Formula I prepared in Example 12.
Figure 6:
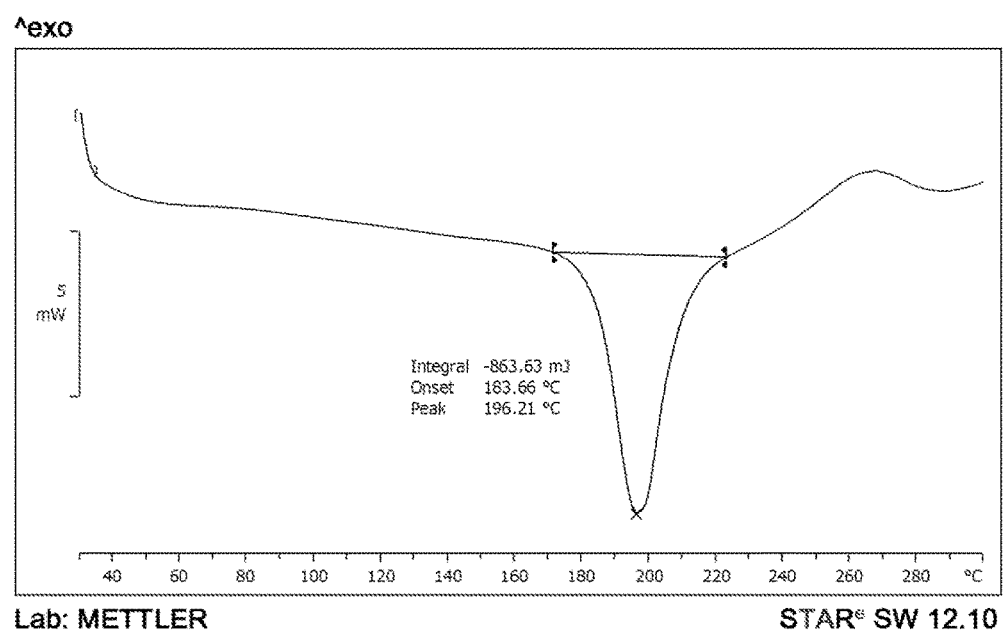
FIG. 6 is a DSC curve of crystal form C of citrate salt of the compound of Formula I prepared in Example 12.
Figure 11:
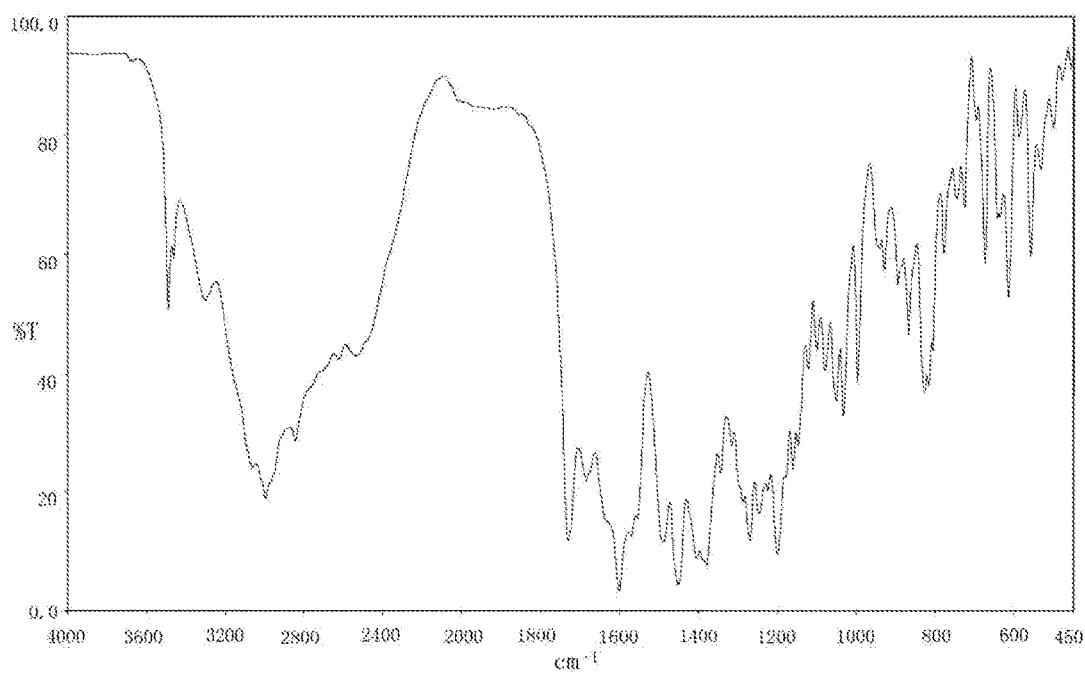
FIG. 11 is an infrared absorption spectrum (IR) of crystal form C of citrate salt of the compound of Formula I prepared in Example 12.

An X-ray powder diffraction pattern thereof with Cu Kα radiation is shown in FIG. 3, a differential scanning calorimetry (DSC) curve is shown in FIG. 6, and an infrared absorption spectrum (IR) is shown in FIG. 11.

Example 13 Preparation of Crystal Form C of Citrate Salt of Compound of Formula I 0.01 mol of the compound of Formula I was dissolved in 90 mL anhydrous ethanol, and a prepared 10 mL of 1.1 mol/L citric acid solution in water was added thereto under refluxing and stirring. After a 1-hour reaction, a solid was precipitated from the reaction mixture. After filtration, the separated solid was refluxed and stirred in ethanol for 1 hour, and filtrated. The separated solid was air-blown dried at 85° C. under ambient pressure, to give crystal form C of citrate salt of the compound of Formula I.

Example 14 Preparation of Crystal Form C of Citrate Salt of Compound of Formula I 0.01 mol of the compound of Formula I was dissolved in 90 mL methanol/water (the volume ratio of methanol to water is 95:5), and a prepared 10 mL of 1.1 mol/L citric acid solution in methanol/water (the volume ratio of methanol to water is 95:5) was added thereto under refluxing and stirring. After a 1-hour reaction, a solid was precipitated from the reaction mixture. After filtration, the separated solid was refluxed and stirred in ethanol for 1 hour, and filtrated. The separated solid was air-blown dried at 85° C. under ambient pressure, to give crystal form C of citrate salt of the compound of Formula I.

Example 15 Preparation of Crystal Form C of Citrate Salt of Compound of Formula I 0.01 mol of the compound of Formula I was dissolved in 90 mL methanol, and a prepared 10 mL of 1.1 mol/L citric acid solution in water was added thereto under refluxing and stirring. After a 1-hour reaction, a solid was precipitated from the reaction mixture. After filtration, the separated solid was refluxed and stirred in ethanol for 1 hour, and filtrated. The separated solid was air-blown dried at 85° C. under ambient pressure, to give crystal form C of citrate salt of the compound of Formula I.

Example 16 Preparation of Hydrochloride of the Compound of Formula I 0.01 mol of the compound of Formula I was dissolved in 90 mL ethanol, and a prepared 5 mL of hydrogen chloride solution in ethanol (10%, w/w) was added thereto under stirring at room temperature. After a 1-hour reaction, a solid was precipitated from the reaction mixture, filtrated and dried in vacuum, to give an off-white solid.

Example 17 Preparation of Sulfate Salt of the Compound of Formula I 0.01 mol of the compound of Formula I was dissolved in 90 mL ethanol, and a prepared sulfuric acid solution in ethanol (10 mL, 1.2 mol/L) was added thereto under stirring at room temperature. After a 1-hour reaction, a solid was precipitated from the reaction mixture, filtrated and dried in vacuum, to give a light yellow solid.

Example 18 Preparation of Malate Salt of the Compound of Formula I 0.01 mol of the compound of Formula I was dissolved in 90 mL ethanol, and a solution of malic acid in 1,4-dioxane (10 mL, 1.2 mol/L) was added thereto under stirring at room temperature. After a 1-hour reaction, a solid was precipitated from the reaction mixture, filtrated and dried in vacuum, to give an off-white solid.

Example 19 Preparation of Maleate Salt of the Compound of Formula I 0.01 mol of the compound of Formula I was dissolved in 90 mL ethanol, and a solution of maleic acid in ethyl acetate (10 mL, 1.2 mol/L) was added thereto under stirring at room temperature. After a 1-hour reaction, a solid was precipitated from the reaction mixture, filtrated and dried in vacuum, to give an off-white solid.

Example 20 Preparation of Tartrate Salt of the Compound of Formula I 0.01 mol of the compound of Formula I was dissolved in 90 mL ethanol, and a solution of tartaric acid in acetone (10 mL, 1.2 mol/L) was added thereto under stirring at room temperature. After a 1-hour reaction, a solid was precipitated from the reaction mixture, filtrated and dried in vacuum, to give an off-white solid.

Example 21 Preparation of Fumarate Salt of the Compound of Formula I 0.01 mol of the compound of Formula I was dissolved in 90 mL ethanol, and a solution of fumaric acid in ethanol (10 mL, 1.2 mol/L) was added hereto under stirring at room temperature. After a 1-hour reaction, a solid was precipitated from the reaction mixture, filtrated and dried in vacuum, to give an off-white solid.

Example 22 Hygroscopicity Test

The compound of Formula I prepared in Example 1, crystal form A of citrate salt of the compound of Formula I prepared in Example 2, crystal form B of citrate salt of the compound of Formula I prepared in Example 8, crystal form C of citrate salt of the compound of Formula I prepared in Example 12, and other salts of the compound of Formula I prepared in Examples 16-21, were tested in accordance with the "Guiding Principles of Drug Hygroscopicity Test" in Appendix XIX J of the 2005 edition of *Chinese Pharmacopoeia*. The hygroscopic weight gain of each of the samples was calculated, and the results are shown in Table 1.

TABLE 1

Results of Hygroscopicity Test

| Compounds | Hygroscopic weight gain (%) |
| --- | --- |
| Example 1 | 2.17 |
| Example 2 | 1.12 |
| Example 8 | 1.79 |
| Example 12 | 1.83 |
| Example 16 | 4.58 |
| Example 17 | 9.85 |
| Example 18 | 7.38 |
| Example 19 | 4.83 |
| Example 20 | 6.08 |
| Example 21 | 5.66 |

The test results indicate that the hygroscopic weight gains of crystal form A, crystal form B, and crystal form C of citrate salt of the compound of Formula I are obviously lower than those of the compound of Formula I and the other salts thereof.

Example 23 Pharmacokinetic Test

In this study, LC-MS/MS was used to determine the plasma concentrations of drugs after the compound of Formula I and crystals of citrate salt thereof were intragastrically administered to Beagle dogs, and the effects of the crystals of citrate salt of the compound of Forumla I on the absorption behavior were observed.

Instrument

The instrumentation system included the LC-10ADvp (Shimadzu, Japan) LC system and the TSQ Quantum Access triple quadrupole tandem mass spectrometer equipped with an electrospray ionization (ESI) source and Xcalibur 2.0.7 data processing system (Thermo Scientific, USA); the operating software was DAS2.1.1; other instruments were One hundred thousandth electronic balance (Mettler Toledo); Centrifugal rotary concentrator (LABCONCO, USA); High-speed refrigerated centrifuge (Model 5430-R, Eppendorf); Refrigerator (Model BCD-281E, Electrolux); Low temperature refrigerator (Model FORMA 700 SERIES, Thermo SCIENTIFIC), etc.

Chromatography Conditions

Column: Thermo C18 LC column (size: 150 L×2.1 mm, 5 μm); column temperature: 40° C.; Mobile phase A: aqueous phase (containing 5 mM ammonium acetate and 0.1% formic acid); mobile phase B: methanol; gradient elution: 0.01 min, 20%; 0.5 min, 20%; 1.5 min, 80%; 4.5 min, 80%, 5 min, 20%, 6 min, stop (phase B). The flow rate was 0.3 mL/min. Benazeprilat was used as the internal standard for measurement.

MS Conditions

The measurement was carried out by LC-MS/MS. The ion source was an ESI source and detection was performed in the positive ionization mode; the spray voltage was 3.8 kV; the heated capillary temperature was 350° C.; the pressure of the sheath gas ($N_2$) was 35 Arb; the pressure of the auxiliary gas ($N_2$) was 15 Arb; and voltages for collision induced dissociation (CID) were 25 eV and 25 eV (internal standard), respectively. The scanning mode was selective reaction monitoring (SRM), and the ion reactions for quantitative analysis were m/z 506.3-315.2 (the compound of Formula I) and m/z 397-351 (internal standard), respectively.

Experimental Method

Six adult healthy beagle dogs, half male and half female, each weighing 9-11 kg, were randomly divided into two groups, and cross-administrated with the compound of Formula I and a crystal of citrate salt thereof.

After fasted for 12 h, the dogs were intragastrically administered with the crystal of citrate salt of the compound of Formula I and with the compound of Formula I (both were formulated with 0.5% CMC-Na as a suspension) at 5.52 mg/kg and 4 mg/kg (equimolar amounts based on the base form), respectively. A blank blood sample was taken before administration; and venous blood samples, about 1.0 ml each, were taken 0.5, 1, 2, 3, 4, 6, 8, 12, 14, 24, 36 hours after administration, placed in test tubes containing heparin, and centrifuged. The plasma fractions were isolated and stored at −80° C. After the washout period (7 days), the two groups of animals were each cross-administrated with the corresponding second drug, and the concentration of compound of Formula I in plasma samples was measured. The plasma concentration-time data for each test animal were input into a computer and the relevant pharmacokinetic parameters were calculated using the pharmacokinetic professional software DAS2.1.1, wherein $C_{max}$ and $T_{max}$ were measured values. $AUC_{(0-t)}$ and $AUC_{(0-\infty)}$ are the area under the plasma concentration-time curve for the period of measurement and the total area under the plasma concentration-time curve, respectively. The $AUC_{(0-t)}$ was estimated by the trapezoidal method from the measured plasma concentrations, and the $AUC_{(0-\infty)}$ was calculated from the $AUC_{(0-t)}$ plus the remaining area in the range t→∞, which can be calculated by the following equation:

$$AUC_{(t-\infty)}=C_t/\lambda$$

In the above equation, $C_t$ is the last plasma concentration measured, and $\lambda$ is the elimination rate constant in the terminal portion of the plasma concentration. The results are shown in Table 2 and Table 3.

TABLE 2

Comparison of average intragastric pharmacokinetic parameters in Beagle dogs

| Parameters | Units | Compounds | |
| --- | --- | --- | --- |
| | | Example 2 | Example 1 |
| $T_{max}$ | h | 2.33 ± 1.03 | 3.17 ± 1.6 |
| $C_{max}$ | μg/L | 63.03 ± 29.22 | 49.97 ± 20.8 |
| $t_{1/2z}$ | h | 5.94 ± 1.59 | 6.71 ± 2.55 |
| $AUC_{(0-t)}$ | μg/L * h | 569.84 ± 342.78 | 501.77 ± 176.25 |
| $AUC_{(0-\infty)}$ | μg/L * h | 586.35 ± 353.48 | 517.3 ± 180.83 |

TABLE 3

Calculated relative bioavailability of the crystal of citrate salt compared to compound of Formula I.

| Relative bioavailability (%) | Example 2 |
| --- | --- |
| $F_1$ | 113.57 ± 68.31 |
| $F_2$ | 113.35 ± 68.33 |

Method for Calculating Relative Bioavailability

The relative bioavailabilities F1 and F2 were calculated with $AUC_{(0-t)}$ and $AUC_{(0-\infty)}$, respectively, by the following equations:

$$F_1=AUC_{(0-t)}(\text{the crystal of citrate salt of the compound of Formula I})/AUC_{(0-t)}(\text{the compound of Formula I})\times 100\%$$

$$F_2=AUC_{(0-\infty)}(\text{the crystal of citrate salt of the compound of Formula I})/AUC_{(0-\infty)}(\text{the compound of Formula I})\times 100\%$$

The experimental results indicate that, the crystal of citrate salt of the compound of Formula I has a better degree and rate of absorption and higher bioavailability, as compared to the compound of Formula I.

Example 24 Stability Test

Crystal form A of citrate salt of the compound of Formula I prepared in Example 2 and Crystal form B of citrate salt of the compound of Formula I prepared in Example 8 were examined in accordance with the "Guiding Principles of Stability Test of APIs and Pharmaceutical Preparations" of Appendix XIX C, Part II of the 2010 edition of *Chinese Pharmacopoeia*. Stability was examined for 10 days under the conditions of 40° C., 60° C., 75% relative humidity (25° C.), 92.5% relative humidity (25° C.), or light illumination (5000 lx±500 lx), respectively. Samples were taken on day 0 and day 10, and the total impurities thereof were assayed by HPLC. The results are shown in Table 4 and Table 5.

HPLC Detection Conditions

Column: Waters XBridge C18 (5 μm, 4.6×150 mm)

Mobile phase A: 0.01 M aqueous ammonium formate, to which 0.1% formic acid was added, and triethylamine was also added to adjust the pH to 7.4

Mobile phase B: acetonitrile

Linear gradient elution, with the following procedure:

| Time (min) | Mobile phase A (%) | Mobile phase B (%) |
| --- | --- | --- |
| 0 | 90 | 10 |
| 35 | 20 | 80 |
| 45 | 20 | 80 |
| 45.01 | 90 | 10 |

Detection wavelength: diode array detector (280 nm)

Flow rate: 1.0 mL/min

Column temperature: 40° C.

Injection volume: 10 μl

Solvent: acetonitrile-water (1:1)

Preparation of the test solution: the solution was taken and accurately weighed, dissolved in a solvent and diluted to a solution at 1 mg per 1 mL, as the test solution.

TABLE 4

Stability of crystal form A of citrate salt of the compound of Formula I

| Conditions | Test period | Total impurities (%) |
| --- | --- | --- |
| Initial state | 0 day | 0.76 |
| 40° C. | 10 days | 0.77 |
| 60° C. | 10 days | 0.89 |
| Relative humidity 75%, 25° C. | 10 days | 0.79 |
| Relative humidity 92.5%, 25° C. | 10 days | 0.77 |
| Light illumination | 10 days | 0.78 |

TABLE 5

Stability of crystal form B of citrate salt of the compound of Formula I

| Conditions | Test period | Total impurities (%) |
| --- | --- | --- |
| Initial state | 0 day | 0.89 |
| 40° C. | 10 days | 0.96 |
| 60° C. | 10 days | 1.19 |
| Relative humidity 75%, 25° C. | 10 days | 0.94 |
| Relative humidity 92.5%, 25° C. | 10 days | 0.95 |
| Light illumination | 10 days | 0.99 |

The experimental results show that both crystal form A and crystal form B of citrate salt of the compound of Formula I have good stability, and the stability of crystal form A is better than that of crystal form B.

What is claimed is:

1. Crystal form A of citrate salt of a compound of Formula I, characterized in that, in an X-ray powder diffraction pattern with Cu Kα radiation, characteristic peaks are present at 2θ angles of 12.78, 14.61, 17.63, 18.98, 21.42 and 23.47 degrees, wherein the compound of Formula I has the following structure, and the molar ratio of the compound of Formula I to citric acid is 1:1,

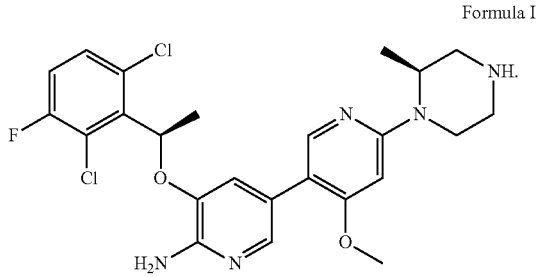 [SMILES: COc1cc(N2CCNC[C@@H]2C)ncc1-c1cnc(N)c(O[C@H](C)c2c(Cl)ccc(F)c2Cl)c1]

Formula I

2. The crystal according to claim 1, characterized by the X-ray powder diffraction pattern substantially as shown in FIG. 1.

3. The crystal according to claim 1, characterized in that the differential scanning calorimetry curve has an absorption peak at about 195.9° C.

4. Crystal form B of citrate salt of a compound of Formula I, characterized in that, in an X-ray powder diffraction pattern with Cu Kα radiation, characteristic peaks are present at 2θ angles of 6.74, 12.62, 18.42, 22.96 and 25.22 degrees, wherein the compound of Formula I has the following structure, and the molar ratio of the compound of Formula I to citric acid is 1:1,

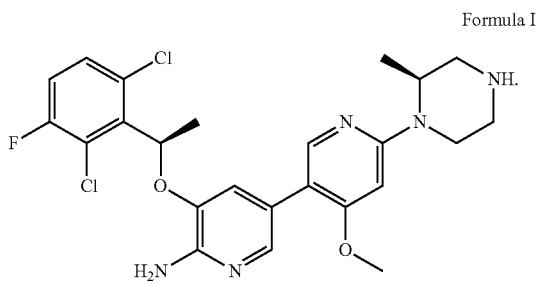 [SMILES: COc1cc(N2CCNC[C@@H]2C)ncc1-c1cnc(N)c(O[C@H](C)c2c(Cl)ccc(F)c2Cl)c1]

Formula I

5. The crystal according to claim 4, characterized by the X-ray powder diffraction pattern substantially as shown in FIG. 2.

6. The crystal according to claim 4, characterized in that the differential scanning calorimetry curve has an absorption peak at about 194.3° C.

7. Crystal form C of citrate salt of a compound of Formula I, characterized in that, in an X-ray powder diffraction pattern with Cu Kα radiation, characteristic peaks are present at 2θ angles of 7.00, 12.78, 13.66, 15.64, 18.14 and 23.43 degrees, wherein the compound of Formula I has the following structure, and the molar ratio of the compound of Formula I to citric acid is 1:1,

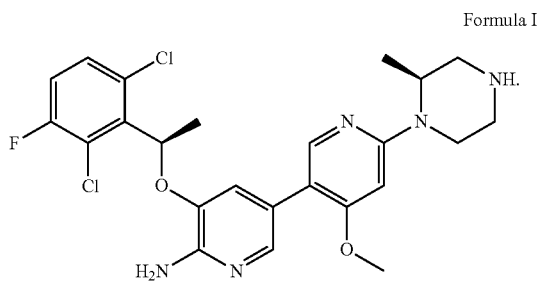 [SMILES: COc1cc(N2CCNC[C@@H]2C)ncc1-c1cnc(N)c(O[C@H](C)c2c(Cl)ccc(F)c2Cl)c1]

Formula I

8. The crystal according to claim 7, characterized by the X-ray powder diffraction pattern substantially as shown in FIG. 3.

9. The crystal according to claim 7, characterized in that the differential scanning calorimetry curve has an absorption peak at about 196.2° C.

10. A pharmaceutical composition comprising a crystal of citrate salt of a compound of Formula I, wherein the crystal of citrate salt of the compound of Formula I is the crystal according to claim 1, the crystal according to claim 4, or the crystal according to claim 7.

11. A method for treatment of an ALK-mediated disease in a subject in need thereof, comprising administrating to the subject a therapeutically effective amount of a crystal of citrate salt of a compound of Formula I, wherein the crystal of citrate salt of the compound of Formula I is the crystal according to claim 1, the crystal according to claim 4, or the crystal according to claim 7; wherein the ALK-mediated disease is selected from the group consisting of ALK-positive non-small cell lung cancer, anaplastic large cell lymphoma, inflammatory myofibroblastic tumor, nasopharyngeal carcinoma, breast cancer, colorectal cancer, diffuse large B-cell lymphoma, systemic histiocytosis, and neuroblastoma.

* * * * *